(12) United States Patent  
Cook et al.

(10) Patent No.: US 9,989,458 B2  
(45) Date of Patent: Jun. 5, 2018

(54) HIGH PRECISION MEASUREMENT OF REFRACTIVE INDEX PROFILE OF CYLINDRICAL GLASS BODIES

(71) Applicant: Corning Incorporated, Corning, NY (US)

(72) Inventors: Ian David Cook, Wilmington, NC (US); Norman Henry Fontaine, Painted Post, NY (US); Qi Wu, Painted Post, NY (US); Jacques Gollier, Redmond, WA (US)

(73) Assignee: Corning Incorporated, Corning, NY (US)

( * ) Notice: Subject to any disclaimer, the term of this patent is extended or adjusted under 35 U.S.C. 154(b) by 105 days.

(21) Appl. No.: 14/928,018

(22) Filed: Oct. 30, 2015

(65) Prior Publication Data

US 2016/0123873 A1    May 5, 2016

Related U.S. Application Data

(60) Provisional application No. 62/073,369, filed on Oct. 31, 2014.

(51) Int. Cl.
```
G01N 21/41      (2006.01)
G01N 21/00      (2006.01)
G01M 11/00      (2006.01)
```
(52) U.S. Cl.
    CPC .......... *G01N 21/412* (2013.01); *G01M 11/37* (2013.01)

(58) Field of Classification Search
    CPC .............................. G01M 11/37; G01N 21/412
    (Continued)

(56) References Cited

U.S. PATENT DOCUMENTS 4,181,433 A    1/1980   Marcuse
4,515,475 A    5/1985   Payne et al.
(Continued)

FOREIGN PATENT DOCUMENTS

DE    68927012    *  1/1997    ............ G01M 11/37
EP    0096829 A1    12/1983
WO    199005904 A1    5/1990

OTHER PUBLICATIONS

D. Marcuse, "Principles of optical fiber measurements," academic Press, New York, 1981, pp. 150-167.
(Continued)

*Primary Examiner* — Sunghee Y Gray  
(74) *Attorney, Agent, or Firm* — Svetlana Z. Short

(57) ABSTRACT

According to some embodiments a method of measuring the refractive index profile of a consolidated glass body having a cylindrical surface comprises the steps of: (a) forming an image of a slit behind the glass body; (b) optionally pre-scanning the cylindrical surface of the test glass body or a reference glass body and analyzing the data within a fixed window to determine the likely location of the zero-order, un-diffracted beam while ignoring other diffracted beams; (c) optionally adjusting the optical power to improve the intensity of the data within the fixed window in order to improve the analysis; (d) predicting the trajectory of the zero-order beam through the preform based on the sampling location $x_i$ (incidence position) of the light impinging on the cylindrical surface and the location at which the zero-order beam impinges on the detector; (e) measuring the cylindrical surface of a glass body while using the estimated location of the zero-order beam and adjusted optical power to set the center of a floating window and the beam power at each measurement point; (e) determining deflection angles of the exiting zero-order beam within the floating window at each sampling location; (e) calculating the refractive index profile (Continued)

of glass body by utilizing a transformation function which determines refractive index at each location based upon the measured deflection angle function of the beam.

20 Claims, 13 Drawing Sheets

(58) Field of Classification Search
USPC .................................................. 356/128, 73.1
See application file for complete search history.

(56) References Cited

U.S. PATENT DOCUMENTS

| | | |
|---|---|---|
| 4,744,654 A | 5/1988 | Jinno et al. |
| 5,078,488 A | 1/1992 | Yamaguchi et al. |
| 5,396,323 A | 3/1995 | Abbott, III et al. |
| 5,450,192 A | 9/1995 | Nolf et al. |
| 5,754,654 A | 5/1998 | Hiroya et al. |
| 2002/0024654 A1 | 2/2002 | Park et al. |

OTHER PUBLICATIONS

PCT International Searching Authority; International Search Report and Written Opinion; Application No. PCT/US2015/057941; International Filing Date Oct. 29, 2015; dated Apr. 7, 2016; pp. 1-13.

\* cited by examiner

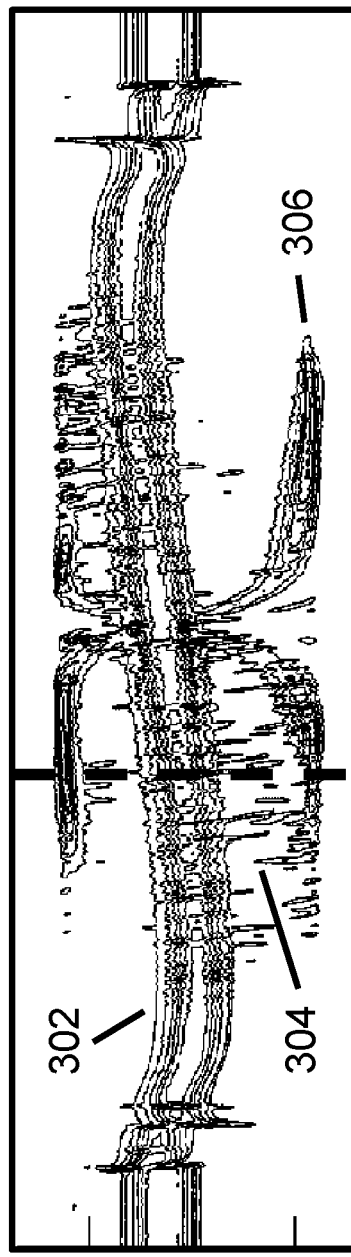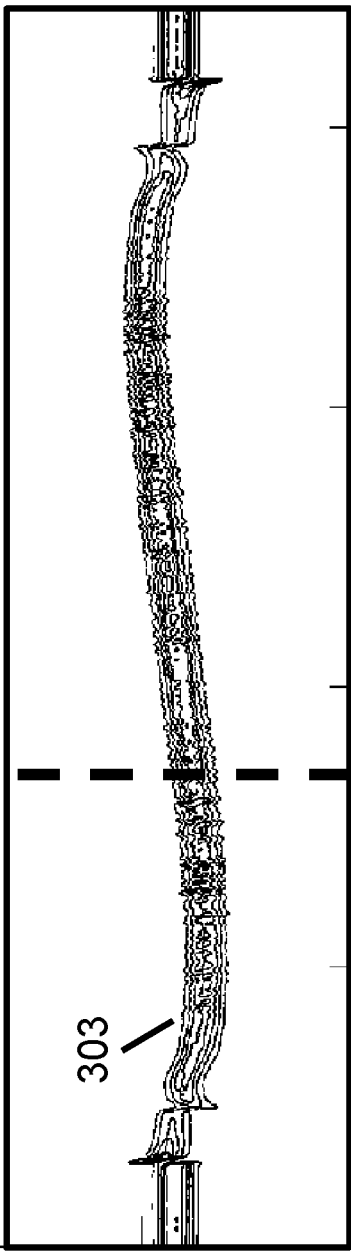

HIGH PRECISION MEASUREMENT OF REFRACTIVE INDEX PROFILE OF CYLINDRICAL GLASS BODIES

CROSS-REFERENCE TO RELATED APPLICATIONS

This application claims the benefit of priority under 35 U.S.C. § 119 of U.S. Provisional Application Ser. No. 62/073,369 filed on Oct. 31, 2014, the content of which is relied upon and incorporated herein by reference in its entirety.

BACKGROUND

The disclosure relates generally to refractive index profile measurements of cylindrical glass bodies and, and more particularly to precision measurements of index profiles of cylindrical glass bodies comprising refractive index striae—i.e., multiple thin layers of glass with rapidly changing indices of refraction.

A light beam passing through a cylindrical glass body can be diffracted into multiple diffractive orders by the thin glass layers, due to refractive index striae, which adversely affect the accuracy and precision of existing refractive index measurement techniques, or can even render the measurement of refractive index profiles impossible.

No admission is made that any reference cited herein constitutes prior art. Applicant expressly reserves the right to challenge the accuracy and pertinence of any cited documents.

SUMMARY

According to at least some embodiments, a method of measuring the refractive index profile of a consolidated glass body with a cylindrical surface, includes the steps of:
  a. scanning the cylindrical surface of the consolidated glass body using an optical beam that emanates from an aperture, such that an image of the aperture is formed downstream from the consolidated glass body, between the consolidated glass body and at least one optical detector, and sampling the cylindrical surface with the optical beam at multiple sampling locations $x_i$;
  b. detecting locations where zero-order optical beams corresponding to the sampling locations $x_i$ impinge on at least one optical detector after passing through the consolidated glass body;
  c. determining deflection angles of the zero-order beams (exiting the consolidated glass body) corresponding to the multiple sampling locations $x_i$;
  d. calculating the refractive index profile of the consolidated glass body based on the deflection angles of the zero-order optical beams corresponding to the multiple sampling locations ions.

According to some embodiments the method further includes the step of predicting the trajectory of the zero-order optical beams through the consolidated glass body based on (i) the sampling location $x_i$ (incidence positions) $x_i$ of the optical beam impinging on the cylindrical surface of the consolidated glass body, and (ii) the locations at which the corresponding zero-order beams impinge on the at least one optical detector.

According to some embodiments the step of calculating the refractive index profile of the consolidated glass body is performed by utilizing a transformation function which determines the refractive index at multiple locations within the consolidated glass body based on deflection angle of the zero-order optical beam corresponding to one sampling location $x_i$ and the deflection angle of zero-order optical beams corresponding to prior sampling locations.

According to some embodiments, wherein the image of the aperture has a width w, and wherein a measurement sampling spacing $\Delta x$ across the cylindrical surface of the consolidated glass body is less than or equal to w; the method further including the step of predicting for each sampling location $x_i$ of the scan, where $x_i=x_{x-1}+\Delta x$, a trajectory of the zero-order beam through the consolidated glass body based on the sampling location $x_i$ of the optical beam impinging on the cylindrical surface and the location at which the zero-order beam is expected to impinge on the at least one optical detector; and discarding from final analysis data for higher order diffracted beams that are detected by the detector.

According to some embodiments, the image of the aperture has a width w, wherein a measurement sampling spacing $\Delta x$ across the cylindrical surface of the consolidated glass body is less than or equal to w; the method further including the step of predicting for each sampling location $x_i$ of the scan, where $x_i=x_{i-1}+\Delta x$, a trajectory of the zero-order beam through the consolidated glass body based on sampling location $x_i$ of the optical beam impinging on the cylindrical surface and the location at which the zero-order beam is expected to impinge on the at least one optical detector; discarding from final analysis data for small angle diffracted beams that are detected by the detector.

According to at least some embodiments, a method of measuring the refractive index profile of an optical fiber preform includes the steps of:
  a. scanning the cylindrical surface of the optical fiber preform through multiple scanning (sampling) locations $x_i$ separated by a distances $\Delta x$, such that $x_i=x_{i-1}+\Delta x$, with an illuminated slit such that an image of the slit is formed behind the optical preform, with the image of the slit having a width w, and $\Delta x<w$;
  b. for each sampling location $x_i=x_{i-1}\Delta x$, predicting a trajectory of the zero-order beam through the preform based on the sampling location $x_i$ of the optical beam impinging on the cylindrical surface of the optical preform and the location at which the zero-order beam is expected to impinge on at least one optical detector;
  c. detecting the location where the exiting zero-order beams corresponding to sampling location $x_i$ impinge on at least one optical detector, and discarding data about higher order diffracted beams and small angle diffracted beams detected by the at least one optical detector for each sampling location $x_i$;
  d. determining the deflection angle of the exiting zero-order beam corresponding to each sampling location $x_i$ of the scan;
  e. calculating the refractive index profile of the preform by utilizing a transformation function which determines the refractive index at each sampling location $x_i$ based on the deflection angle of the beam corresponding to that location and other scanned sampling locations $x_i$ that are adjacent to $x_i$ but greater in distance from the center of the preform.

According to one embodiment a method of measuring the refractive index profile of an optical preform having an axis and a cylindrical surface, includes comprising the steps of:
  a. optically projecting through the cylindrical surface of the optical preform an image of an illuminated slit oriented at an angle between 10° and 80° to the axis of the preform such that an image of the slit is formed behind the optical preform;

b. detecting the image of the illuminated slit where it has been formed behind the optical preform.

c. the slit being configured such that the illuminated slit is projected through entire width of the optical preform;

d. processing the detected image to determine the location of an zero-order beam;

e. determining the deflection angle of the zero-order beam corresponding to each sampling location $x_i$ in the detected image f. calculating the refractive index profile of the preform by utilizing a transformation function which determines the refractive index based on the deflection According to some embodiments the deflection function based refractive index measuring method results in a much improved precision and capability of measuring refractive index profiles having significant striae structures in a consolidated fiber preform, including OVD preforms.

One of the advantages of the embodiments of the present invention is that it provides accurate refractive index profile measurements of cylindrical glass bodies, for example of fiber optical preforms, and more particularly that these methods enable precision measurements of the refractive index profile of the those preforms that are used to make high bandwidth multimode optical fibers.

One of the advantages of the embodiments of the present invention is that it provides accurate refractive index profile measurements of cylindrical glass bodies, for example of fiber optical preforms, even if the majority of the scanning beam energy is diffracted by striae.

One of the advantages of the embodiments of the embodiments of the present invention is that it provides accurate refractive index profile measurements of cylindrical glass bodies, for example of fiber optical preforms with striae structures that are uniform (homogeneous) in the axial direction.

Additional features and advantages will be set forth in the detailed description which follows, and in part will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

FIGS. 3A and 3B are contour plots of the integrated intensity profiles at every sampling location $x_i$ in the scan of optical fiber preforms, using an optical refractive index measurement system designed to operate at wavelength of 3.39 µm;

FIG. 3C illustrates data corresponding to a cross-section of FIG. 2A taken near the radius r=⅓a;

DETAILED DESCRIPTION

Figure 1A:
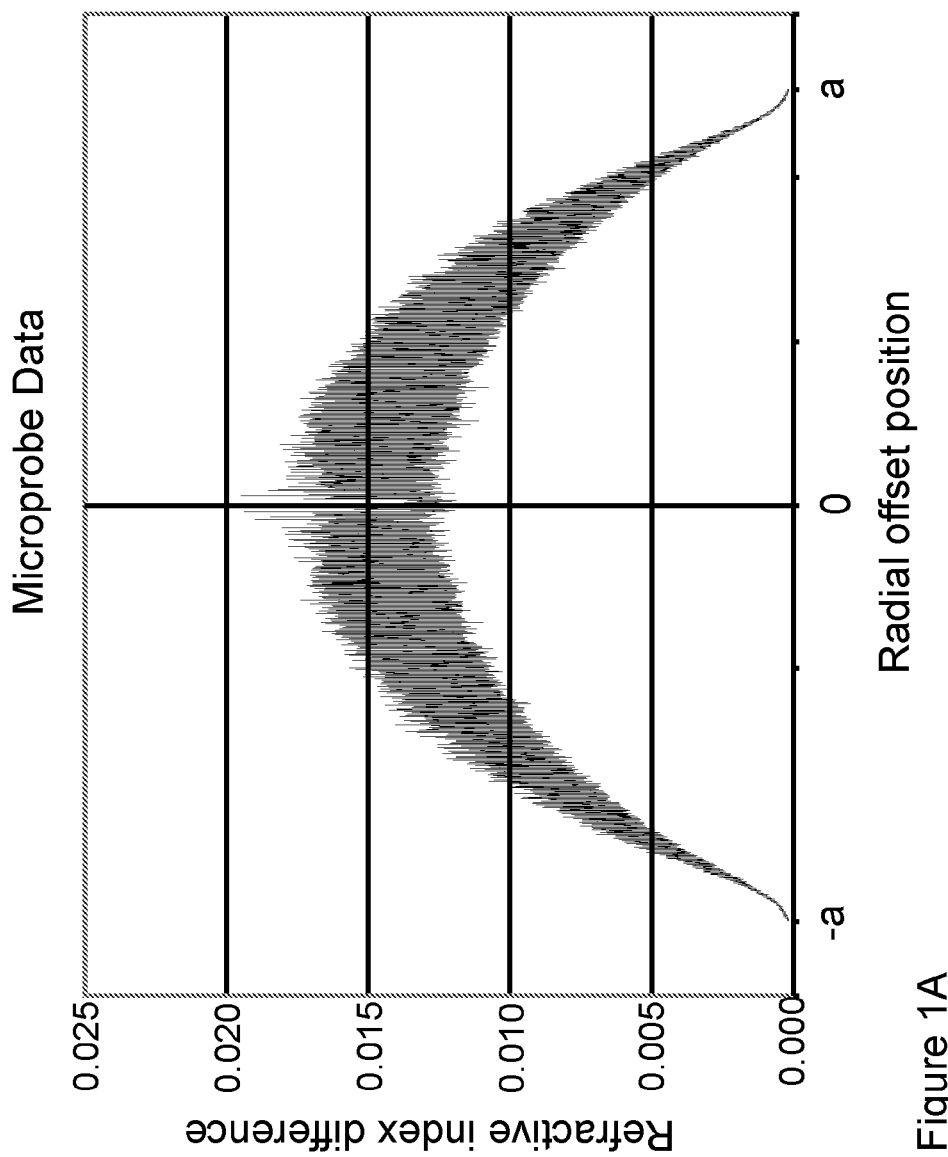
FIG. 1A illustrates a computed refractive index profile of an exemplary optical fiber preform made by a OVD process.

Bandwidth is a measure of the maximum data transmission capability of a fiber. The bandwidth of a multimode fiber (MMF) is highly sensitive to the refractive index profile variations in the optical fiber. Therefore, the refractive index profile of the fiber should be precisely controlled during the production of a fiber. It is desirable when manufacturing a MMF to generate the smoothest possible gradient in the refractive index profile of the fiber by precision laydown of the updoped silica soot (e.g., $GeO_2$ doped silica soot) as it is deposited onto the fiber preform. It is also desirable, in the manufacturing of MMFs, to precisely measure the refractive index profiles of consolidated optical fiber preforms and to draw fiber using only the preforms with the desired refractive index profiles. In addition, the information on the measured refractive index profile can be fed back to the preform soot laydown process to maximize the rate of production of high quality fiber preforms while minimizing waste. This maximizes the yields of high quality optical fibers.

The striated structures or striae in cylindrical consolidated glass bodies are thin layers of glass with variations of refractive index. A consolidated optical fiber preform is a cylindrical consolidated glass body, from which an optical fiber is drawn. Optical fiber preforms that are made by OVD (outside vapor deposition) process comprise a large number of thin layers of glass with variations of refractive index (different indices of refraction at different radial positions). A light beam passing through a cylindrical glass body, such as a consolidated optical preform made by an OVD process can be diffracted into multiple diffractive orders by the thin glass layers, due to refractive index striae.

A combination of the large amplitude of refractive index variations within the consolidated glass and the spacing of such index variations from one glass (deposition) layer to the next determines the existence and strength of the diffractive effect when a beam of light of a particular wavelength $\lambda$ propagates through the optical preform made, for example, by the OVD process. It is noted that OVD manufactured preforms have striae structures that are substantially uniform in the axial direction (i.e., substantially homogeneous along the preform's length).

For example, the optical preform may be created when hot glass soot is deposited as a thin layer on top of previously layered soot layers as a precursor materials (e.g., silica and Ge) are fed to the burner and the burner traverses (passes over) the length of the soot preform and deposits glass soot over the previously laid soot layer. However, the deposition of Ge/Si is non-uniform within each layer, creating thin bands of varying refractive index in the consolidated glass preform (i.e., after the glass soot preform has been fully sintered). Thus, the multi-pass soot deposition process for producing optical preforms typically leads to refractive index striae throughout the cross-section of the consolidated preform. This is illustrated for example, FIGS. 1A and 1B).

Figure 1B:
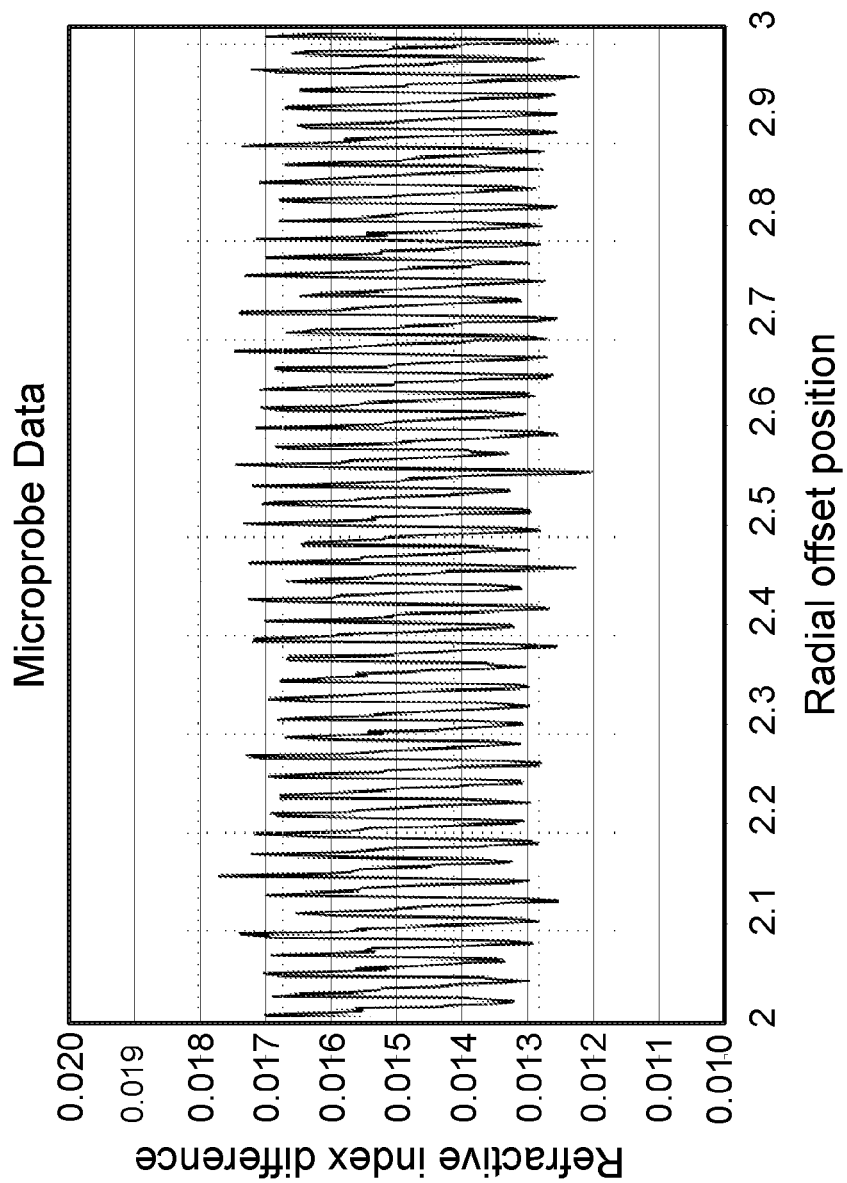
FIG. 1B is an enlarged portion of the refractive index profile shown in FIG. 1A, which illustrates the striae within the optical preform.

More specifically, the striae are where the refractive index profile of the cylindrical (consolidated) glass body has many local maxima and minima, forming periodic (or variable period) structures. FIG. 1A illustrates refractive index variations in a cylindrical glass body, in this embodiment a consolidated glass optical fiber preform, as a function of radial position from the preform's center line. This exemplary optical fiber preform was made by an OVD process, and the refractive index profile was obtained by a destructive microprobe measurement technique, which measures the weight percentage of $GeO_2$ in a compositional analysis of a cross-section of the preform and relates it to refractive index. FIG. 1B depicts an expanded portion of FIG. 1A, where the refractive index variations are shown at a radial positions of 2 to 3 mm from the preform's center. In FIG. 1B the refractive index variations are depicted as refractive index difference, relative to the refractive index of pure (i.e., undoped) silica.

The refractive index profile of consolidated glass preform (or a similar cylindrical glass body) can be determined by scanning an optical beam through the consolidated glass of the preform's body, and measuring the deflection angle of the refracted optical beam exiting the preform. However, the refractive index striae in consolidated glass preforms (cylindrical consolidated glass bodies), can affect the accuracy and precision of deflection angle measurements at certain transverse beam launch locations during the scan. This happens because the striae function as a transmissive diffraction grating. That is, for certain optical beam trajectories through the optical preform, the wavelength of the light may resonantly interact with the periodicity of the striae and the phase matching of these interactions can lead to multiple, strongly and weakly diffracted optical beams of different diffraction orders. Each of those beams can experience additional diffractions along the trajectory through the preform and as the beam traverses the cross-section of the preform it encounters the striae at varying angles, as well. The net result is that many diffracted optical beams may exit the preform at more than one angle. These diffracted optical beams may be created and they may exit the preform in addition to a purely refracted, un-diffracted beam (zero-order beam). In some instances nearly all of optical power in the incident beam is diffracted into higher order beams making the zero-order beam difficult to detect. In other instances the angle of the diffracted beams (vs. that of the un-diffracted beam) is so small that they impinge on the detector very close to the same locations as the zero-order beam and the finite width of the diffracted beams overlap with the zero-order beam. Hence these diffractive effects can lead to errors in the determined deflection angle of the zero-order beam's axis. If the zero-order beam becomes too weak for the detector to detect, it may also render it impossible to determine the deflection angle. We discovered that these inaccuracies can make it very difficult to precisely construct the entire refractive index profile of some preforms from the measured deflection function data obtained using commonly utilized refractive index measurement systems.

The following are embodiments of the optical system (100), and the method(s) utilized for measuring refractive indices of optical preforms, that improve the accuracy of the measured refractive index profiles. The embodiments described herein utilize the optical beam deflection function of the zero-order beam for non-invasive index profile measurement of optical preforms and other cylindrical bodies that have refractive index striae. According to some exemplary embodiments the method and optical system utilize a visible wavelength source. According to other exemplary embodiments the method and optical system utilizes a near Infra Red (e.g., $\lambda<2$ µm, or $\kappa<1$ µm, for example 0.78 µm to 2 µm, or 0.78 µm to 1 µm) light source that is incoherent or has low coherence, which sufficiently eases the diffracted effect on near IR beams due to striae, to allow the measurement of zero-order beam deflection function with higher precision.

One method for characterizing the refractive index profile of cylindrical glass bodies such as optical preforms is based upon a beam deflection function measurement technique. This method measures or determines the total deflection angle of an un-diffracted optical beam (also referred to herein as a zero-order beam), after it has propagated through the cylindrical body (e.g., consolidated optical preform (414)) in a direction that is transverse to the preform's axis. This deflection angle is acquired at a plurality of launch positions $x_i$ (also referred to herein as beam incidence position, incident location, scanning location, offset location, or sampling location $x_i$) as the optical beam (413) or preform (414), is translated in a direction that is also transverse to the center axis of the optical preform, scanning the beam across the cylindrical surface of the preform. That is, the incident optical beam scans across the cylindrical surface of the glass preform, refracts through the body of the preform, and exits the preform at different deflection angles, corresponding to different sampling location $x_i$. In the embodiments described herein the translation is along the x-axis, and the position of the incident scanning beam (sampling position $x_i$) across the preform is incremented by the amount(s) $\Delta x$. The accumulated series of deflection angle measurements produces the deflection angle function of the un-diffracted optical beam exiting the preform vs. transverse beam launch position (i.e., vs. the sampling locations $x_i$, where $x_i = x_{i-1} + \Delta x$) and this can be transformed into the refractive index profile using mathematical transformation, for example, the Abel transformation, also referred to herein as Abel transform (eq. (1)):

$$n[r(x)] = n(a)\left[1 + \frac{1}{\pi}\int_x^a \theta(t)/\sqrt{t^2 - x^2}\, dt\right], \quad (1)$$

where a is the outer radius of the preform, n(a) is the refractive index of the medium surrounding the consolidated optical preform, r(x) is the distance of closest approach to the preform's axis and θ(t) is the measured deflection angle at offset location t, where t is an integration variable that ranges from x to a. Since the measured value for the refractive index of the consolidated optical preform at a particular inner radial location x depends on the measured deflection angles between that point and the preform's outer radius a, any errors that occur in the measurement of the deflection angle at that point will also impact the accuracy of the remaining refractive index measurements between that point and the preform's axis. For typical optical fiber preforms that are weakly refracting, the approximation of r(x)≈x (where x is the off-set position of the optical beam impinging on the preform, relative to the axis of the preform) is valid.

Figure 2A:
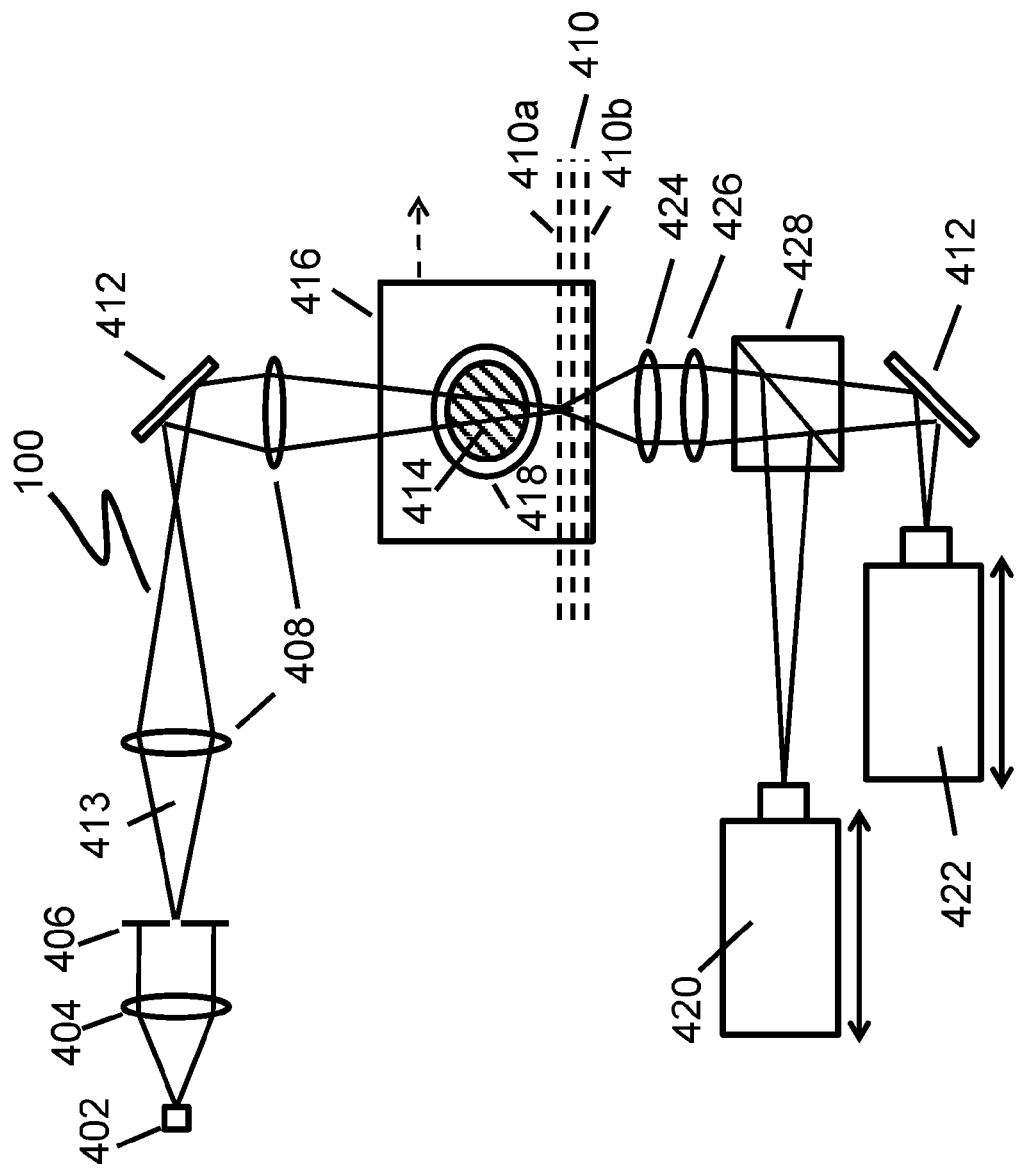
FIG. 2A is a schematic diagram of an exemplary embodiment of an optical NIR (near infrared wavelength) refractive index profile measurement system.

FIG. 2A is a schematic illustration of one exemplary embodiment of the refractive index measurement system (100) that utilizes a scanning optical beam (413) to measure the refractive index profile of the consolidated cylindrical glass body, for example the optical preform (414). The optical beam (413) scans across the cylindrical surface of the consolidated glass body and impinges on the surface at multiple predetermined locations $x_i$ separated by distance(s) Δx. For example, in at least some of the exemplary embodiments described herein the center of the scanning optical beam is incident on the glass surface at locations $x_i$. (It is noted that distance Δx can be constant across the scan, or can vary depending on the beam position on the surface of the preform.) After propagating through the glass (e.g., the body of the preform 414) the optical beam (413) forms a zero-order beam and the diffracted higher order beam portions. We detect or determine locations where the zero-order optical beams (corresponding sampling locations $x_i$) that exit the cylindrical glass body (such as the optical preform) impinge on the optical detector ((420) and/or (422), e.g., a camera), and then determine deflection angles of these exiting zero-order beams corresponding to the multiple sampling locations $x_i$. We then calculate the refractive index profile of the consolidated glass body by determining refractive indices at multiple locations within the consolidated glass body, based on their measured deflection angles of the zero-order optical beams corresponding to the multiple sampling locations $x_i$.

In some embodiments the optical system (100) is a NIR (Near Infrared) system (i.e., the scanning optical beam has a wavelength between 0.7 and 2 μm (e.g., 0.705 μm, 0.73 μm, 0.785 μm, 0.853 μm, 0.94 μm, 0.98 μm, 1.064 μm, 1.31 μm, 1.55 μm, 1.65 μm, or therebetween). Laser diode light sources operating in these wavelengths are commercially available, for example, from Thorlabs, Inc of Newton, N.J. Other wavelengths, for example, visible light (0.4 μm to 0.7 μm) or MID-IR may also be utilized. For example, the light source may operate in the NIR or in the visible wavelength, where the light source wavelength is 0.4 μm≤λ≤2 μm, and have low coherence, with coherence length CL of 0.001 mm≤CL≤10 cm, for example 0.1 mm≤CL≤10 cm, or 1 mm≤CL≤1 cm. Such low coherence can advantageously improve the measurement accuracy of the refractive index measurement system (100).

Figure 2B:
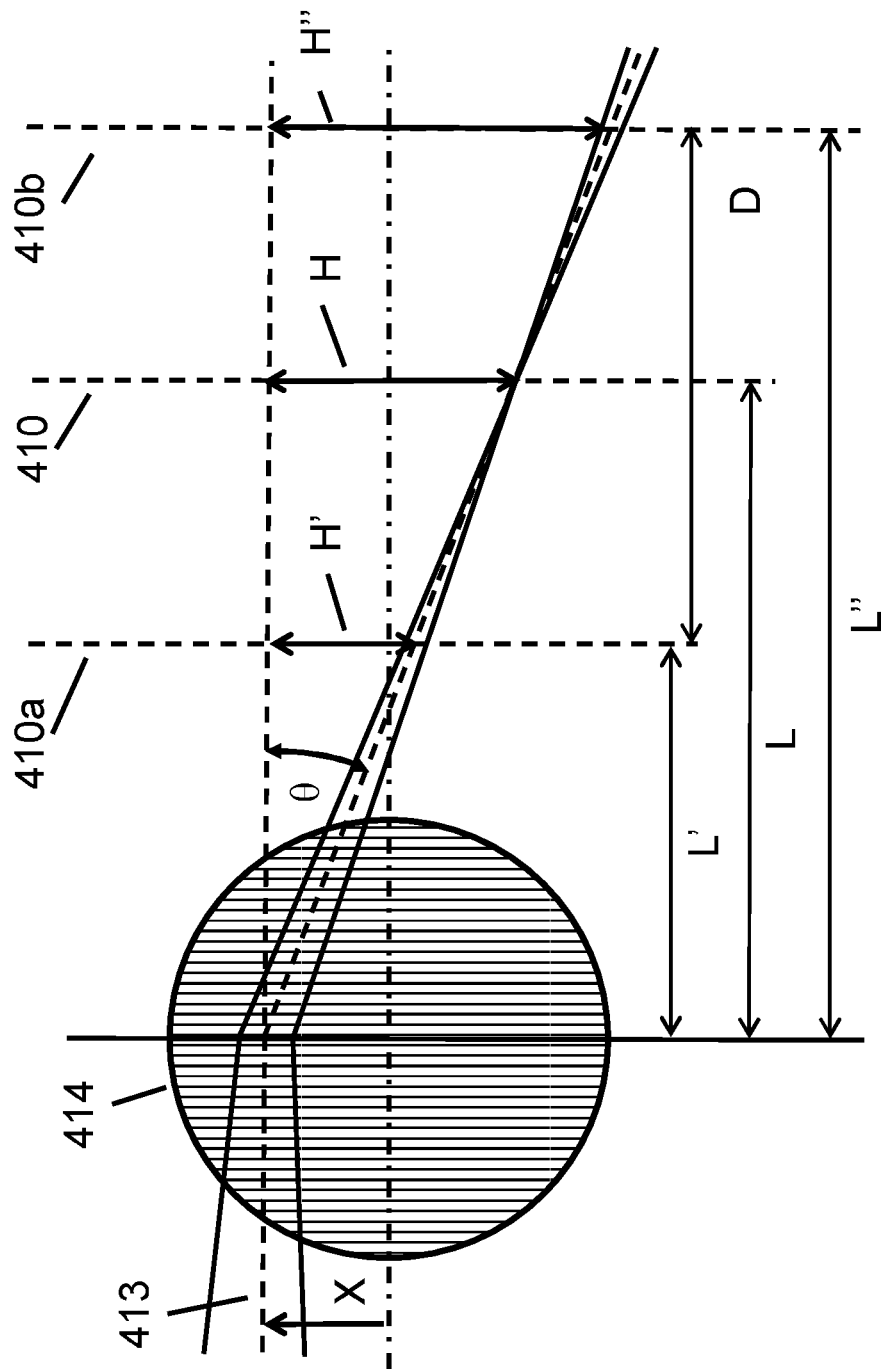
FIG. 2B is a close up illustration of the locations of the preform and the object planes for both detectors for the exemplary NIR system.

FIG. 2B is a close up illustration of the locations of the consolidated optical preform (414) and the object planes for each detector in the embodiment shown in FIG. 2A. As shown in FIGS. 2A and 2B, the optical system (100) of this exemplary embodiment comprises a light source (402) that together with a lens (404) provides a substantially collimated optical beam to an aperture (406), illuminating the aperture. According to this embodiment, the image of the aperture (402) is formed at or near the object plane(s) (410), adjacent to detector's object planes (410a), and/or (410b) (that are formed by the lenses (424), (426) that re-image this image of the aperture onto one or more detectors (420), (422)). Thus, the optical system (100) forms the image of the aperture on one or more detectors (420), (422). In this embodiment lenses (424), (426), in conjunction with one another provide the reimaging function, so that the image of the aperture (406) is formed on the detector(s). The information provided by the un-diffracted (zero order) beam(s) on detector(s) is used to calculate the deflection angles $\theta(x_i)$ of the exiting un-diffracted beams, in order to determine the refractive index profile of the preform (or of a similar cylindrical glass body). If one detector is utilized, the image of the aperture (406) is formed near the plane (410) which is also the object plane (410) of the lens(es) that re-image this image of the aperture onto the detector (420). If multiple detectors are utilized, the image of the aperture (406) can be formed near the image plane (410) or adjacent to the object plane (410a) or (410b) of the lens(es) that will re-image or relay this image of the aperture on the active surfaces of the detectors (420), (422). In the exemplary embodiment shown in FIGS. 2A and 2B, the light source (402) is a square LED (402') emitting light from an area that is 0.3 mm×0.3 mm at the central wavelength of 940 nm and having a spectral width of 40 nm—i.e., it provides illumination in a 920 nm to 960 nm wavelength range, centered at 940 nm. (FIG. 2A). In this embodiment the angular emission from the LED (402') is 120 degrees at the FWHM intensity level. In this embodiment the lens (404) has a focal length of 50 mm. Lens (404) collimates this light and provides it to an aperture (406), which in this embodiment is a 100 μm wide×25.4 mm tall (long) chrome-on-glass slit (406'). However, the slit or the aperture may have other dimensions, for example, the slit could be as short as 100 μm (e.g., the dimensions of the slit can be 100 μm×100 μm). The maximum usable aperture height—i.e., the maximum usable length of the light that emanates from the slit is determined by the height of the projected image of the slit onto the active surface of the detector(s). In this embodiment the illuminated length of the slit (406') is purposely set so that the height of its image (approximately 25.4 mm) greatly overfills the height of the detector's active area, which is approximately 6.6 mm high. This is done in order to use only the most intense light coming from the central area of the length of the slit.

Other alternative aperture shapes can also be utilized. The slit could be a physical light blocking structure with a fixed-width air gap aperture, or it could be a controllable-width slit that can be varied by electronic control or manual mechanical means. A long slit, such as the one described above could be utilized, or alternatively a line of multiply stacked slits with beam blocks in between them may also be utilized for the purposes of measuring multiple deflection functions along the axis of the preform in a single scan.

Another exemplary embodiment is to utilizes a tapered slit wherein the slit is narrow at one end and broad at the other. This would provide an advantageous effect in improving detection and/or resolution of the zero-order beams on the detector(s) because the resultant image of the slit on the detectors could be cross sectioned and analyzed piecewise, choosing a portion of the image that has the best compromise between the optical power and the diffraction from the edges of slit. (It is desirable to make the slit width as small as possible without compromising optical power on the detector and without introduction of edge-diffraction from the slit. The aperture or slit with the tapered width has at least a portion of its width that is wide enough to allow enough optical power to fall on the detector, while minimizing diffraction from its edges.) If a single slit (406') has a tapered width, such, then software could analyze subsections of the image to allow the collection of data from multiple points along the axis of the preform while performing just one scan. In the case of a stack of multiple slits, each slit could have a different width, where generally the width would vary between 50 µm and 200 µm. This balances the need to minimize diffractive effects from the slit edges (which cause beam divergence) and the desire to measure with a narrow beam in order to obtain the smallest spatial resolution possible within the preform.

For example, the aperture or a slit with the tapered width may have a length between 100 µm and 25 mm long and a width w'(z) which changes from narrow to wide such that 50 µm≤w'≤200 µm, For example, the slit width may gradually increase from a minimum width w' of 50 µm to a maximum width w' of a 200 µm. Also for example, the slit width may gradually increase from a minimum width w' of 75 µm to a maximum width w' of a 150 µm.

The single slit (406') in the embodiment shown in FIGS. 2A and 2B is centered on the collimated beam with the long axis of the slit parallel to the axis of the preform and has a width w' (which in this embodiment is 100 µm). The light source(s), for example LED (402') and the lens (404) have been chosen such that the substantially collimated optical beam has a divergence angle that is less than the diffraction angle that arises from the diffraction generated from the edges of the slit (406').

As shown in FIG. 2A, in this embodiment, two lenses (408) each with an effective length of 100 mm form a 4f system that telecentrically relays the image of the illuminated slit (406') onto an image plane (410). More specifically, FIG. 2A illustrates that in this embodiment the image of the slit is not situated inside the optical preform. The image of the aperture 406 is formed downstream of the consolidated glass body (e.g., preform 414), between the consolidated glass body and at least one optical detector. The image of the slit has a width w. Mirror(s) (412) are used to fold the optical path in order to decrease the footprint of the optical system 100. The optical system and the consolidated optical preform (414) are moved relative to one another (e.g. left to right, as indicated by the dashed arrow in FIG. 2A) so that the optical beam (scanning optical beam) moves across the surface of the preform (414).

In this embodiment the preform under test (414) is mounted inside a measurement cell (416) with the cavity between the cell and the preform being filled with index matching oil (418). An example of this oil could be an immersion oil with refractive index near to that of the silica cell and the preform, such as supplied by Cargille Laboratories of Cedar Grove, N.J. The preform (414) of this embodiment is constructed with mean striae periodicity d (or spacing d) that ranges from 1 to 15 µm (e.g., consolidated glass layer thickness of 1 to 15 µm). This striae periodicity (spacing d) is achieved by controlling the laydown thickness per pass, which are chosen to help the measurement system measure the deflection angle of the zero-order beam within acceptable error limits despite diffractive effects. The striae spacing d is measured at or adjacent to the radial position r within the preform, where r is situated in: ⅓≤r/a≤⅔, preferably at r/a=½, where a is the outer radius of the preform.

In this embodiment, the measurement cell (416) is a square plate made from fused silica that has a circular hole (416A) drilled through it. The hole has a diameter that is only a few millimeters larger than the diameter of the preform (414). The optical cell has parallel entrance and exit surfaces, and all surfaces through which the beam passes are optically polished.

The plane (410) where the image of the slit is formed (image plane) is located at a position beyond the preform, and in this embodiment downstream of the hole in the cell (416), so that all the necessary beam refractions through the preform have occurred prior to the beam crossing the image plane. More specifically, in this embodiment, the image plane (410) lies inside the material of the cell, approximately 5 mm beyond the edge of the hole. In another embodiment a measurement cell is not used and the preform is located in a chamber that is filled with index matching oil. In that embodiment, the requirement for the location of the image plane of the slit is simply that it lies beyond the preform (downstream).

In this exemplary embodiment, it is necessary to further relay that image of the aperture or the slit onto the detector (s) (420 and 422), since the image plane 410 of the slit lies physically within the fused silica cell. In this embodiment, the detectors (420 and 422) are, for example, cameras that have 1936×1458 pixels with an individual pixel size of 4.54 µm and good response to near infrared wavelengths (700-1000 nm). It can be appreciated that the physical width of the pixelation of the measured data from any detection method need be sufficiently small to ensure that the image of the zero-order beam at the detector is adequately sampled. Generally, it is desirable to have the pixelation of the detector to be 10 times smaller than the width of the image of the zero-order beam at the detection plane (detector face). If a single detector (420 or 422) is used, then it is necessary to precisely know the distance from the center of the preform (414) or the cylindrical glass body to the image plane (410) in order to calculate the deflection angle, (FIG. 2B)

$$\theta = \tan^{-1}\left(\frac{H}{L}\right) \quad (2)$$

Since consolidated optical preforms (or other cylindrical glass bodies) are not always perfectly straight along their length and may have some curvature, the distance between the preform axis and the image plane of the slit or aperture (406) can vary each time the preform (or anther cylindrical glass body) is inserted into the cell (416). A precision positioning system can be used to precisely locate the axis of the preform at the preferred distance from the detector each time it is inserted. In this embodiment, that problem is solved by the use of two identical detectors, such as two identical CCD cameras, for example.

In this embodiment the relay lens system for each camera comprises two lenses (FIG. 2A), one lens (lens 424) with a 75 mm focal length, and the other lens (lens 426) with a 150 mm focal length. These lenses are positioned such that they create a 2:1 magnification of the aperture's (slit's) image situated at the detection plane of each camera (camera face, or the active surface of the detector). A beamsplitter (428) is employed so that both cameras (or detectors) can view the image of the slit. The positions of cameras are adjusted individually so as to separate the locations of the object planes (410a, 410b) being observed by each camera. In this embodiment, the object plane of each camera (410a) and (410b) lies at a different location inside the cell. Since the numerical aperture of the beam incident on the preform is very small (because the light impinging on the aperture (406) is collimated or nearly collimated) and the depth of field of the optical system is (100) very large, the images of the slit that are observed by both detectors (cameras) are only slightly (i.e., insignificantly) distorted even though the slit's image is not located precisely at the object plane of either camera. Hence a determination of the zero-order beam's axis positions (or centroids) on both detectors (for example cameras (420, 422)) can be accurately determined. Knowledge of the difference in the image plane positions D of the cameras enables a more accurate determination of the deflection angle of the zero-order beam (see, for example, FIG. 2B)

$$\theta = \tan^{-1}\left(\frac{H'' - H'}{L'' - L'}\right) \quad (3)$$

In this exemplary embodiment the distance between the object planes of the two cameras is 1 mm, however it could range between 0 mm and 5 mm. Preferably, object planes of the two detectors are situated by 0 mm to 5 mm offset from the aperture image plane and are not in the same location, because this helps to unambiguously measure the deflection angle of the zero-order beam, without the need to know the distance between the object plane of detector relative to the preform.

In this embodiment, a low-coherence LED light source is used in order to avoid or to minimize speckle interference from diffuse scattering and interference between the zero-order beam and the diffracted beams, which in at least some embodiments advantageously and significantly improves the measurement stability, and accuracy of results.

As discussed above, the optical beam, illuminates a narrow slit, which is imaged onto the camera sensor (detector 420, 422). According to the embodiments of the method described herein, the optical system (100) forms the image of the aperture (406), such as a slit (406') behind the cylindrical consolidated glass body, for example at or adjacent to the detector's object plane (410a, 410b) and thus concentrates (or focuses) all of the optical beams exiting the glass body into their smallest size (i.e., smallest width or spot diameter). This helps to separate the small-angle diffracted beams from the zero-order beam when they impinge on the detector(s). In contrast, in conventional systems, the image of the source would sit at the plane of the preform's axis, as such the zero-order beam and the diffracted beams associated with small angle diffraction in conventional systems would be wider and would overlap the zero-order beam more than in the embodiments of the optical system (100) disclosed herein. That, in turn, makes it more difficult for conventional measurement systems to distinguish the undiffracted beam from the diffracted beams, and this leads to increased measurement error. The imaging of the slit provides a way to better distinguish the zero-order beam transmission through the cylindrical consolidated glass body (e.g., preform) from the diffracted orders.

The embodiments of the optical system (100) when used with near IR or visible wavelength sources can measure refractive indices of optical preforms with a thinner pass thickness and small striae periodicity (or striae separation) d≤12 μm, and especially refractive indices of optical preforms (and other cylindrical glass bodies) with d≤10 μm (and thus smaller angles of diffraction) more accurately than can be achieved by conventional systems.

According to at least some embodiments, the methods of measuring the refractive index profile of a consolidated glass body with a cylindrical surface utilize a pre-scan step (also referred to herein as a pre-scan phase) to determine the approximate location of the zero-order beam(s) on the detector(s). During the pre-scan phase of the measurement, according to some embodiments, the preform or a reference preform of similar size and refractive index profile is measured using a fixed windowing method (see window 508 in FIG. 4B) which could be, for example, about 80 pixels wide. This window is centered in the middle of the camera. All data due to the optical beams falling outside of this window is ignored or discarded because it is known that the zero-order beam will strike the camera or detector within this window. The optimum width of the window can be determined empirically, by trial and error, with the main emphasis placed on balancing the rejection of the small and large angle diffraction from the analysis and ensuring that the zero-order beam is not rejected. If a reference preform is utilized, this is done once to determine the location of the zero order beam (e.g., the location of the zero-order beam's axis) corresponding to each sampling location $x_i$, and then the pre-scan data can be used for other similarly designed preforms.

As the pre-scan progresses, the optical power of the light source (such as LED for example) is varied to keep, for example, the maximum number of integrated intensity counts at approximately 80% of pixel saturation level on the detector (s), within this window. For example, this would be approximately 200 average counts per horizontal pixel in the integrated intensity data if the detector were saturating at 255 counts. This ensures that the image of the aperture or a slit is best-resolved even for cases where strong diffraction removes most of the optical power from the zero-order beam and it ensures that the zero-order beam does not saturate the camera's pixel depth. In this embodiment, the light source's (e.g., LED's) drive current is recorded for each offset measurement position (i.e., for each sampling location $x_i$) along with the determined central axis of the zero-order beam. One exemplary method for determining the central axis of the zero-order beam is to calculate the centroid using only data that lies within the window and above a minimum threshold level. This threshold level is set to exclude data that lies below it, and thus excludes the low-level signal from the undesirable small angle diffraction (504). Nominally this threshold is 50% of the maximum of the peak counts associated within the window and would be a level of about 100 counts for this example.

During the measurement scan phase (i.e., after the optional pre-scan phase, for example), the LED or light source's drive current for that position is read in and set on the (LED) controller, thus setting the optical power of the zero-order beam to the optimum level for analysis. The position of the central axis of the beam that was found in the pre-scan phase is read in, or otherwise calculated, and that is used to set the center position of the window. Thus the window for the measurement scan is allowed to float and it ensures that the center of the zero-order beam is approximately centered in the window in which data is analyzed. This floating window method leads to a more accurate determination of the zero-order beam's central axis than what would be obtained using a fixed window. The floating window of the measurement scan does not need to be the same width as the fixed window of the pre-scan.

An alternative to the pre-scan step is to use pre-existing knowledge about the general shape of the deflection function to determine the expected location of the zero-order beam. This can be in the form of an array of expected locations determined by theoretical means, or by means of predictive curve fitting to previously measured points in order to determine the expected location of the next point to be measured.

Thus, an exemplary embodiment of a method of measuring the refractive index profile of a consolidated glass body having a cylindrical surface (e.g., an optical preform made by an OVD process) comprises the steps of:

I. Utilizing a light source to provide light within a specified wavelength, and forming with this light an image of a slit behind the glass body;

II. Utilizing an optional pre-scanning step that includes: (a) pre-scanning the cylindrical surface of the test glass body or a reference glass body by the optical beam utilizing the light provided by the light source; (b) forming an image of the slit on at least one detector and analyzing the data (obtained during the pre-scanning of the cylindrical surface) within a fixed window on the at least one detector to determine the likely location of the zero-order, un-diffracted optical beam that is impingent on the at least one detector while ignoring other, diffracted beams; (c) optionally adjusting the optical power of a light source (during the pre-scan step) to improve the intensity of the detected power corresponding to the zero-order beam within the fixed window, in order to improve the ability to resolve the zero-order beam and the signal-to-noise ratio;

III. Predicting the trajectory of the zero-order beam through the preform based on the incidence position of the light impinging on the cylindrical surface (i.e., sampling location $x_i$) and the location at which the zero-order beam impinges on the detector;

IV. Scanning across a glass body while using the predicted location of the zero-order beam to set the center of a floating window and adjusting the optical power to the predetermined optimal level corresponding to each measurement point (each sampling location $x_i$);

V. Determining deflection angles of the exiting zero-order beam within the floating window at each sampling location $x_i$; and VI. Calculating the refractive index profile of glass body by utilizing a transformation function which determines refractive index at each location based upon the measured deflection angle function of the optical (zero-order) beam.

Thus, according to some embodiments the optical power provided by the light source is dynamically adjusted at each sampling location $x_i$, for example in order to avoid reaching detector saturation by the zero-order beam while keeping the intensity of the zero-order beam strong enough, so that it can be detected by the detector. For example, the light intensity on the detector may be adjusted to be between 200 nW and 200 mW.

According to at least some embodiments, a method of measuring the refractive index profile of a consolidated glass body with a cylindrical surface, includes the steps of:
a. scanning the cylindrical surface of the consolidated glass body using light emanating from an aperture (optical beam, also referred to herein as a scanning optical beam) such that an image of the aperture is formed downstream of the consolidated glass body, between the consolidated glass body and at least one optical detector, and thus sampling the cylindrical surface with the scanning beam at multiple sampling or scanning locations $x_i$ separated by distance $\Delta x$;
b. determining locations where the zero-order optical beams corresponding to each of the sampling locations) impinge on the optical detector after passing through the consolidated glass body;
c. predicting the trajectory of the zero-order optical beams through the consolidated glass body based on the incidence positions $x_i$ (also referred to herein as sampling location) of the scanning optical beam impinging on the cylindrical surface of the consolidated glass body and the locations at which the corresponding zero-order beams impinge on the detector;
d. determining deflection angles $\theta(x_i)$ of the exiting zero-order beams corresponding to the multiple sampling locations $x_i$; and
e. calculating the refractive index profile of the consolidated glass body, for example by utilizing a transformation function which determines refractive index at multiple locations within the consolidated glass body based on the deflection angle of the zero-order optical beam corresponding to one sampling location and the deflection angle $\theta(x_i)$ of zero-order optical beams corresponding to prior sampling locations $x_i$.

According to some embodiments, for example, a method of measuring the refractive index profile of a consolidated glass body with a cylindrical surface, includes the steps of:
a. scanning the cylindrical surface of the consolidated glass body with an optical beam incident on the illuminated aperture having a width w', such that an image of the aperture is formed behind the optical preform, with the image width of the aperture w, and measurement sampling spacing $\Delta x$ across the preform, where the optical beam scans across the cylindrical surface at multiple incidence locations (sampling locations) $x_i$, where $x_i = x_{i-1} + \Delta x$ and $\Delta x \leq w$;
b. for each sampling location $x_i$ of the scan, predicting a trajectory of the zero-order beam through the preform based on the incidence position of the light (of the optical beam) impinging on the cylindrical surface of the preform and the location at which the zero-order beam is expected to impinge on the optical detector;
c. detecting the location where the exiting zero-order beam impinges on the detector, preferably discarding from the analysis any higher order diffracted beams that may be detected by the detector for each sampling location;
d. determining the deflection angle of the exiting zero-order beam corresponding to each sampling location $x_i$ of the scan; and
e. calculating the refractive index profile of the preform by utilizing a transformation function which determines the refractive index at each sampling location $x_i$ based on the deflection angle of the beam corresponding to that location and on all measured locations that are adjacent to $x_i$ but are greater in distance from the center of the preform.

According to some embodiments, for example, a method of measuring the refractive index profile of an optical preform having a cylindrical surface includes the steps of:
a. scanning the cylindrical surface of the optical preform with an illuminated slit such that an image of the slit is formed behind the optical preform, with the image size w of the slit, and measurement sampling spacing $\Delta x$ across the preform, and $\Delta x < w$;
b. for each sampling location $x_i = x_{i-1} + \Delta x$ of the scan, predicting a trajectory of the zero-order beam through the preform based on the incidence position of the light (of the optical beam) impinging on the cylindrical surface of the preform and the location at which the zero-order beam is expected to impinge on the at least one detector;

c. detecting the location where the exiting zero-order beam impinges on the at least one detector, discarding from the analysis any higher order diffracted beams that may be detected by the at least one detector for each sampling location;

d. determining the deflection angle of the exiting zero-order beam corresponding to each sampling location $x_i$ of the scan;

e. calculating the refractive index profile of the preform by utilizing a transformation function which determines the refractive index at each sampling location $x_i$ based on the deflection angle of the zero-order beam corresponding to that location and on all measured locations that are adjacent to $x_i$ but greater in distance from the center of the preform.

According to the exemplary embodiments, step size(s) Δx for the scan (distance Δx) is generally kept to be between ½ and ⅛ of the minimum width w of the slit's image. This is done in order to avoid under-sampling across the preform while avoiding excessive measurement time and added expense.

In some embodiments, the transformation function is an Abel transform.

The number i of sampling locations may be, for example 500<i<2000. For example, in some embodiments 800<i<1500.

In some embodiments scanning is performed with a slit image of width w, and sampling spacing Δx such that w/8≤Δx≤w/2. In some embodiments the slit is between 100 μm and 25 mm long and has a width w from 50 μm to 200 μm, and sampling spacing Δx such that w/8≤Δx≤w/2.

In some embodiments, the slit is 100 μm to 25 mm long and of varying (changing) width w'(z) along the direction of the axis of the preform z. I.e., the slit has a tapered width varying, for example, from about 50 μm to about 200 μm and forming an image of width w(z). In order to avoid under-sampling of the data of the scan the sampling spacing Δx is such that: (⅛ of the minimum slit width)≤Δx≤½ minimum slit width). As described above, example, the slit's image width w may be 50 μm<w<200 μm, and Δx<w/2.

According to some embodiments, an optical system (100) similar to that shown in FIGS. 2A and 2B is utilized, but the optical beam is not scanned across the surface of the consolidated preform. Thus, this embodiment does not utilize the moving stage that moves the optical beam and the consolidated optical preform relative to one another. Instead, the length of the slit is chosen such that it allows the optical beam propagating through its length to cover simultaneously the entire width of the optical preform. According to this embodiment, a method of measuring the refractive index profile of an optical preform having a cylindrical surface includes the steps of:

a. optically projecting through the cylindrical surface of the optical preform an image of an illuminated slit oriented at an angle between 10° and 80° to the axis of the preform such that an image of the slit is formed behind the optical preform, wherein the slit is long enough such that the light propagating through the slit spans the width of the entire preform;

b. detecting the image of the illuminated slit where it has been formed behind the optical preform;

c. sectioning the image of the slit using an appropriate software, and analyzing each section independently;

d. processing the image of the slit to detector in order to determine the location of an zero-order beam (and preferably discarding from the analysis: (i) any higher order diffracted beams that may be present in the image of the slit on the detector(s) and/or (ii) small angle diffracted beams that may be present in the image of the slit on the detector(s));

e. determining the deflection angle of the zero-order beam corresponding to each sampling location $x_i$ (corresponding to each section of the image) in the detected image f. calculating the refractive index profile of the preform by utilizing a transformation function which determines the refractive index based on the deflection angles of the zero-order beam exiting the optical preform. (For example, calculating the refractive index profile of the preform by utilizing a transformation function which determines the refractive index based on the deflection angles of the zero-order beam exiting the optical preform corresponding to each section of the image).

For example, according to some embodiments of the slit (406') is rotated so that the light beam intercepts the fiber preform at about a 45° angle, which enables capture of the beam deflection information at varying radial positions without the need for a scanning stage. The angular orientation is an optimization of the slit length, angle of orientation, and image magnification. This angular orientation allows capture of the deflection function for the entire preform without a scanning stage. A further enhancement of the angular orientation may include, for example, addition of an intensity mask (e.g., a neutral density filter of variable attenuation) to equalize the intensity and sharpness across the image.

As discussed above, striae results in diffraction of optical beams propagating through the preforms. If the periodicity of the striae (or spacing between the striae) is d, and the measurement wavelength is λ (i.e., the wavelength of the optical beam propagating through the preform), then the 1st order diffraction angle φ (internal to the preform) of the optical beam is described by eq. 4, below:

$$\phi = \sin^{-1}\left(\frac{\lambda}{d}\right) \qquad (4)$$

For example, a preform that has been produced by the OVD process may have a nominal striae spacing d (or periodicity d) of about 14.1 μm at the radial location r/a=½. If a visible or near infrared (NIR) wavelength beam (0.9 μm<λ<2 μm) passes through such an optical preform, the first-order diffraction angle from these striae is small (e.g., 3.7°<φ<8.2°. If such a preform is measured with a NIR beam in a conventional far-field measurement configuration system, then the expanding diffracted beams can overlap with the expanding zero-order, un-diffracted beam at the detector, making the measurement of the zero-order beam's deflection angle inaccurate.

Small angle diffraction is diffraction that occurs near or adjacent to the un-diffracted beam, at diffraction angles smaller than those of the first-order diffraction, for example at <3° relative to the un-diffracted beam (and often or angles below 2°, or below 1°). As striae periodicity or spacing d decreases, the diffraction angles of small angle diffraction will also increase, further reducing the overlap of the zero-order beam with the diffracted beams produced by the small angle diffraction. Thus, reducing striae periodicity or making the spacing d smaller can advantageously improve the accuracy of the measured zero-order beam deflection angle function, and hence the refractive index profile that is obtained by the measurement.

One strategy that solves this problem is to increase the angular dispersion of the diffracted beams to enable better detection of the un-diffracted zero-order beam by use of a longer wavelength mid-infrared (Mid-IR) beam, for example at a wavelength of 3.4 µm. If the wavelength of the optical beam is 3.4 µm, then utilizing this Mid-IR wavelength increases the first-order diffraction angle φ to, for example, 14.0°, which is sufficient to separate the un-diffracted zero-order beam from the diffracted beams at the detector. This makes it easier to reject their influence on the determination of the deflection angle of the zero-order beam's central axis by use of analytical or physical techniques such as windowing. This, in turn, makes it possible to accurately track only the deflection angle of the zero-order beam throughout the entire scan.

Another strategy that provides a solution to this problem is to utilize visible or Near IR light sources, when the cylindrical glass body such as the consolidated optical preform has the striae spacing d<12 µm (for example d<12 µm). That is, to accurately track the deflection angle of the central axis of the zero-order beam, the optical the preforms can be made with smaller striae separations (i.e., more, but thinner passes) and then measured by the optical system (100) that utilizes visible or Near IR light sources. The two activities of laying down the soot and of measuring the refractive index of the optical preform are interrelated because the method of laydown can adversely impact the ability to accurately measure the preform and the measurement system must be designed to accurately measure the types of preforms that are being produced. Changing the soot laydown process or the measurement system design or both can lead to a lower cost production of fibers with improved performance. Decreasing the pass thickness of the soot laid onto the preform, leads to a decrease in the periodicity of the striae or (or striae spacing d). Decreasing the striae spacing d (or striae periodicity distance d) is another way of increasing the first-order diffraction angle, thus weakening the diffractive effects of the striae. Decreasing the pass thickness has an additional benefit in that it also improves control over the mean smoothness of the refractive index profile in the drawn fiber. However, decreasing the pass thickness means that the total number of passes will also be increased in order to make the same size preform. We found that the refractive index measurements, when performed with optical beams having wavelength λ<2 µm (e.g., λ<1 µm) advantageously provide the most accurate results when striae spacing d (and thus the thickness of glass layers within the consolidated preform) satisfies d<12 µm (e.g., 2 µm≤d≤12 µm), and most preferably d<10 µm,—e.g., when 3 µm≤d≤10 µm, or 4 µm≤d≤10 µm. The striae spacing is measured at or adjacent to the radial position r within the preform, where r is situated in: ⅓≤r/a≤⅔, for example r/a=½, and a is the outer radius of the preform.

The magnitude of the optical power P within the higher diffraction order(s) is a function of pass thickness which directly corresponds to striae periodicity d, striae index perturbation amplitude δn, and wavelength λ, specifically:

$$P \propto \left[\frac{(\delta n)(d)}{\lambda}\right]^2. \quad (5)$$

Hence diffraction effects in preform measurements can be reduced by: 1) decreasing the index perturbation (δn), 2) decreasing the pass thickness (thus decreasing striae spacing d), 3) increasing the light wavelength (λ) of the optical beam, or 4) a combination of these three factors. During our analysis, when we compared the methods using optical preforms made by OVD processes with differing pass thicknesses, the refractive index perturbation δn of the consolidated glass preforms remained constant (only the net volume of material deposited via each pass was changed (reduced). The pass thickness was allowed to decrease (i.e., glass layer thickness n associated with each pass during preform laydown was decreased), resulting in smaller striae spacing d.

For example, we performed refractive index measurements of two exemplary consolidated glass preforms, both with a MID-IR optical beam (3.28 µm) and a near IR optical beam (0.94 µm). The two exemplary preforms were made with an OVD process. They were: 1) a preform with a 14.1 µm mean pass thickness after consolidation (thick pass glass deposition process, layer thickness=14.1 µm, or striae spacing d=14.1 µm), and 2) a preform with 6.7 µm mean pass thickness after consolidation (thin pass process, striae spacing d=6.7 µm). Thus, in these exemplary embodiments the mean striae separation d (also to referred herein as striae periodicity, or striae spacing) of these optical preforms was 14.1 and 6.7 µm, respectively. (Typically, unless specified otherwise, in the embodiments described herein, the nominal value for the mean pass thickness (after the glass been consolidated), or striae separation d, is taken at the location of the consolidated preform's radius of r/a=½, where a is the outer radius of the preform). It is noted that the value d corresponding to striae separation slowly changes across the diameter of the preform.

We discovered that when the optical preform or a cylindrically shaped consolidated glass body is being scanned by an optical beam (when its refractive index profile is being determined) the decrease in the striae spacing d significantly and advantageously results in an increase of the angles of diffraction of the optical beam(s) traversing the preform under measurement, which makes it easier to make the accurate refractive index measurements because the first order and higher order diffracted beams are well off-set from the zero-order beam. See, for example, Table 1, examples A and B, (λ=3.39 µm), which shows the first-order diffraction angle increasing from 13.9° to 30.5° when the value d was reduced which means that the first order and higher orders of the diffracted beams are better separated from the zero-order beam in the camera images. Table 1 also depicts relative diffracted optical power and calculated first-order diffraction angles for measurement system wavelengths λ=0.940 µm (case examples C and D) when measuring preforms made using thick pass and thin pass soot laydown processes. Table 1, examples C and D, shows that the first-order diffraction angle increased from 3.8° to 8.1° when the value d was reduced from 14.1 µm to 6.7 µm, which means that the first order and higher orders of the diffracted beams are better separated from the zero-order beam across the entire scan range. In Table 1, below, the striae spacing d corresponds to r/a=½, and the index perturbation δn was the same for all cases, and it was simply normalized to the value of 1, for convenience.

TABLE 1

| Case | δn | d (μm) | λ (μm) | P (Diffracted Power in arbitrary units) | Normalized Diffracted Power (case A = 1) | 1st Order Diffraction Angle (degrees) |
|---|---|---|---|---|---|---|
| A | 1 | 14.1 | 3.39 | 17.30 | 1 | 13.9 |
| B | 1 | 6.7 | 3.39 | 3.91 | 0.23 | 30.5 |
| C | 1 | 14.1 | 0.94 | 225.00 | 13.01 | 3.8 |
| D | 1 | 6.7 | 0.94 | 50.80 | 2.94 | 8.1 |

Additionally, the relative power P lost by the zero-order beam to diffraction for the preforms made by the thinner pass process decreases, in contrast to the power P which was lost for the preforms made by thicker pass process, (for example to 23% in example B vs. example A, at measurement wavelength λ=3.39 μm). Thus, the decrease in pass thickness (layer thickness, or striae periodicity d to 12 μm or less and more preferably to 10 μm or less) improves the ability to accurately measure the zero-order beam deflection angle function and hence the refractive index profile that is obtained by the measurement because more optical power is concentrated into the zero-order beam.

This improvement is illustrated by a comparison of the integrated light intensity data from the detector, as measured at each offset position $x_i$ of the scanning optical beam across the preform, for both the example thick pass (preform consolidated glass layer thickness of 14.1 μm, or d=14.1 μm, FIG. 3A) and the example thin pass preform (consolidated glass layer thickness of 6.7 μm, d=6.7 μm, FIG. 3B). These scans were both obtained using the Mid-IR preform measurement system, similar to that shown in FIG. 2A.

Figure 3C:
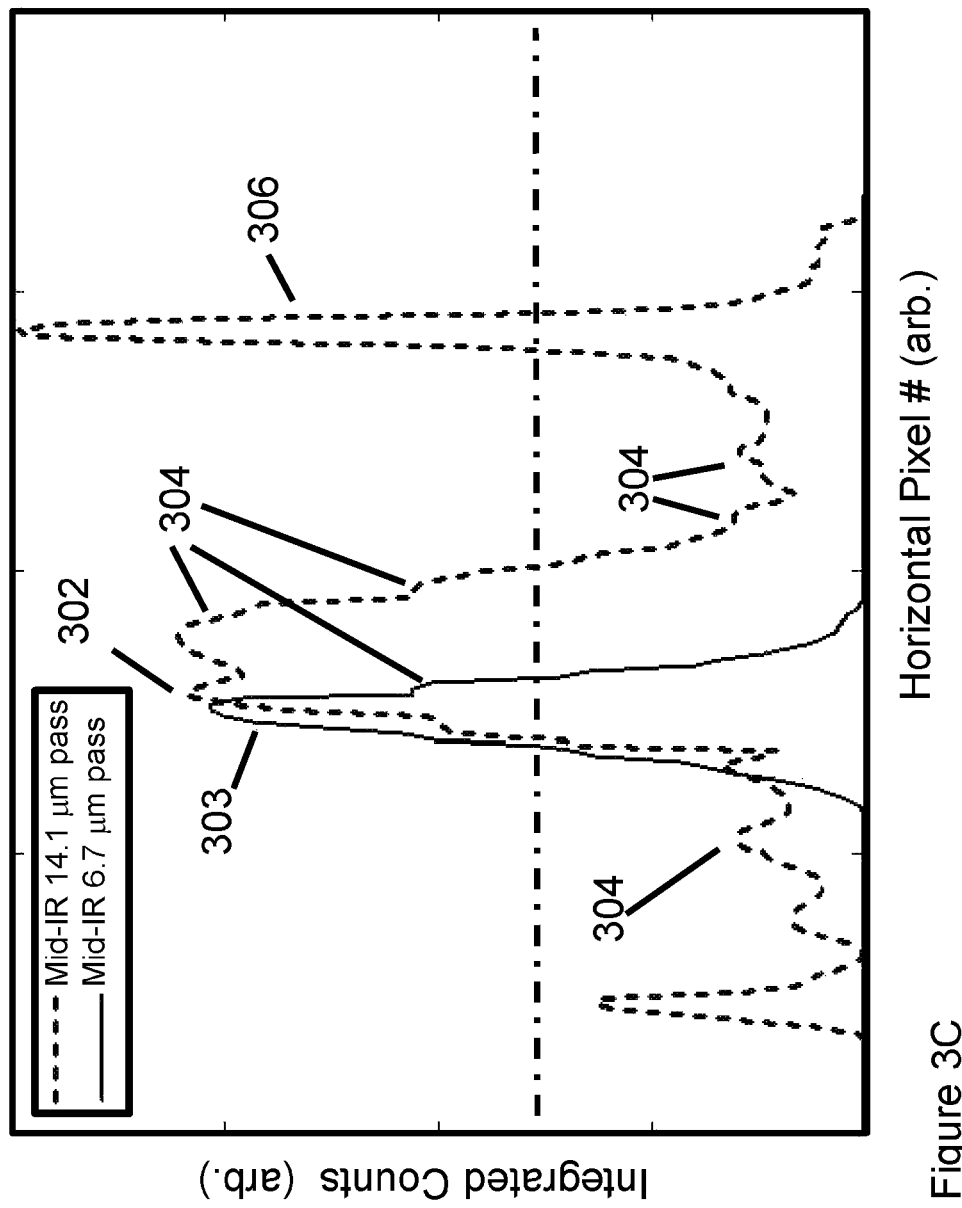

More particularly, FIG. 3A illustrates a contour plot comprised of the integrated intensity profiles from the camera images at every offset location $x_i$ of the scan of the preforms that were made with a thicker pass (d=14.1 μm) and with a thinner pass (d=6.7 μm), using a refractive index measurement system designed to operate at the Mid-IR beam wavelength of 3.39 μm. As seen from FIG. 3A, zero-order beam 302 occupies the central region of the scan and corresponds to the preform with 14.1 μm thick pass layers. FIG. 3B illustrates a zero-order beam 303 that also occupies the central region of the scan, and corresponds to the preform with d=6.7 μm. FIG. 3A illustrates that small angle diffracted beams (304) are overlapping and/or are situated close to the zero-order (un-diffracted) beam. For example, small angle (304) diffraction is observed to be overlapping with the zero-order beam. The vertical dashed line in FIGS. 3A and 3B corresponds to one of the locations where clearly resolving the un-diffracted or zero-order optical beam is difficult and where errors can occur in the determined refractive index profile FIG. 3C illustrates an integrated light intensity profile of the scanning laser beam as it impinges on the detector, at a specific offset $x_i$ from the axis of the preform (taken near to the radius r=⅓a, and expressed in integrated counts across detector pixels), corresponding to the dashed line of FIGS. 3A and 3B. The vertical dashed line in FIGS. 3A and 3B indicates a location of integrated counts (integrated intensity) cross-section shown in FIG. 3C.

The dashed lines of FIG. 3C correspond to the preform with thick pass layers (d=14.1 μm), and the solid lines to the preform with thinner pass layers (d=6.7 μm). FIG. 3C also illustrates that the zero-order (un-diffracted) optical beam is more easily observed or detected when it propagates through a preform with thinner glass layers (i.e., through a preform made with smaller pass thickness (or layer width), that has smaller striae periodicity (or separation d) than the zero-order beam propagating through the preform that has thicker glass layers (i.e., through a preform made with larger pass thickness, that has a larger periodicity d). However, this figure also illustrates that in preforms with thicker pass thickness (e.g., d>14 μm, and even d>12 μm), when using Mid IR light and detector, the zero-order beam 302 can overlap with the small-angle diffraction beams 304, and may be hard to resolve (i.e., difficult to detect). This is an example of a problematic region for the refractive index measurement where the light due to small angle 304 diffraction is observed to be strongly overlapping with the zero-order beam, which in the embodiment of FIG. 3A is situated at a radial location of the preform near to r/a=⅓. (Note, a is the outer most radius of the consolidated glass preform.)

More specifically, FIG. 3C illustrates the measured amplitude of a signal on the detector corresponding to the dashed location in FIGS. 3A and 3B, which correspond to the optical beam propagating near to the radius r=⅓a where the diffraction problem for the thick pass preform is the worst. In order to improve the detection accuracy of the zero-order beam, we utilized a 50% level intensity computational filter to reject low level diffraction from the analysis (dash-dot line). That is, in this exemplary embodiment, all data that are below the threshold level of 50% (dash-dot line) is discarded from the analysis before determining the axis or location of the zero-order beam. FIG. 3A also illustrates that in this embodiment of the preform, with the thicker pass layers (d=14.1 μm), the large angle diffraction 306 is strong, but is of little concern because it does not overlap with the zero-order beam. FIGS. 3A, 3B and 3C illustrate that the small angle diffraction that over-laps the zero-order beam is stronger for the thick pass preform as compared against the thin pass preform. The small angle diffraction in the thick pass preforms can lead to a greater error in determining the deflection angle of the zero-order beam at each point in the measurement of the thick pass preform. In comparison, the thin pass deflection curve is narrower, with much weaker diffraction overlap between small angle diffraction beam and the zero-order beam. This, in turn, leads to less error in determining the deflection angle of the zero-order beam. This improvement, resulting from the reduction of pass thickness (reduction in layer thickness) directly increases the accuracy in the measured refractive index profile that is calculated from the deflection function.

The measurements corresponding to FIGS. 3A, 3B and 3C were performed with use of a mid-IR beam (3.39 μm) and a mid-IR optical detector. However, a mid-IR optical detector is intrinsically a thermal detector, thus the precision of measuring an IR beam's central axis is very sensitive to the ambient environmental stability. Even slight changes in temperature can affect the measurement accuracy, which negatively impacts the accuracy of the measured refractive index profile. Thermal detectors are inherently electronically noisier than NIR and visible light detectors. These phenomena can further limit the ability to accurately determine the zero-order beam deflection angle at the detector. Furthermore, speckle present in mid-IR optical beams provided by highly coherent light sources further limits position detection sensitivity. Generally the MID-IR lasers such as the MID-IR HeNe lasers have coherence lengths of meters. We discovered that the use of a low coherence beam is preferred. Such low coherence beams can be provided, for example, by a laser diode, an LED, or a broad spectrum lamp; the coherence length of the laser diode being on the order of 1 cm, the LED being on the order of 100 micrometers, and a broad spectrum lamp being a few micrometers. A broad spectrum lamp can be used in conjunction with a bandpass filter to decrease the spectral width of the beam.

Thus, we realized that it may be advantageous if the Mid-IR measurement system detector could be replaced with a low noise silicon, or InGaAs, or Ge based detector and if the highly coherent light sources could be replaced with a low coherence, NIR (near IR) or visible light source (e.g., such as an LED or a bandpass filtered broad spectrum lamp).

When we utilized a light beam of NIR wavelength<1 µm for the preform's refractive index measurements in conjunction with silicon based detectors, we discovered that the amount of optical power due to diffraction for the thick pass preform (d>12 µm) would be greater than the power loss due to diffraction when using the Mid-IR system. For example, when we utilized a light beam of NIR wavelength of 0.94 µm for the preform's refractive index measurements in conjunction with silicon based detectors, we discovered that the amount of optical power diffracted from the zero-order beam for the thick pass preform is about 13 times greater than when using the Mid-IR system with a beam wavelength $\lambda$ of 3.39 µm (Table 1, cases A and C). Additionally, the first order diffraction angle decreases from 13.9° to 3.8°, and the diffraction angles due to small angle diffraction decrease as well.

In contrast, a NIR measurement of a thin pass preform (d<10 µm) would have a normalized diffracted power of only 2.94 times greater than the normalized diffracted power when using the Mid-IR system with a beam wavelength of 3.39 µm, and the first order diffraction angle is 8.1° (Table 1, cases B and D). This indicates that measuring a thin pass preform with a near IR or with a visible wavelength optical beam is advantageous, but that measuring a thick pass preform (d>12 µm) may be difficult when using wavelengths<1 µm, and that utilizing mid IR wavelengths with an optical system similar to that shown in FIG. 2A may be preferable for such thicker pass preforms.

Figure 4A:
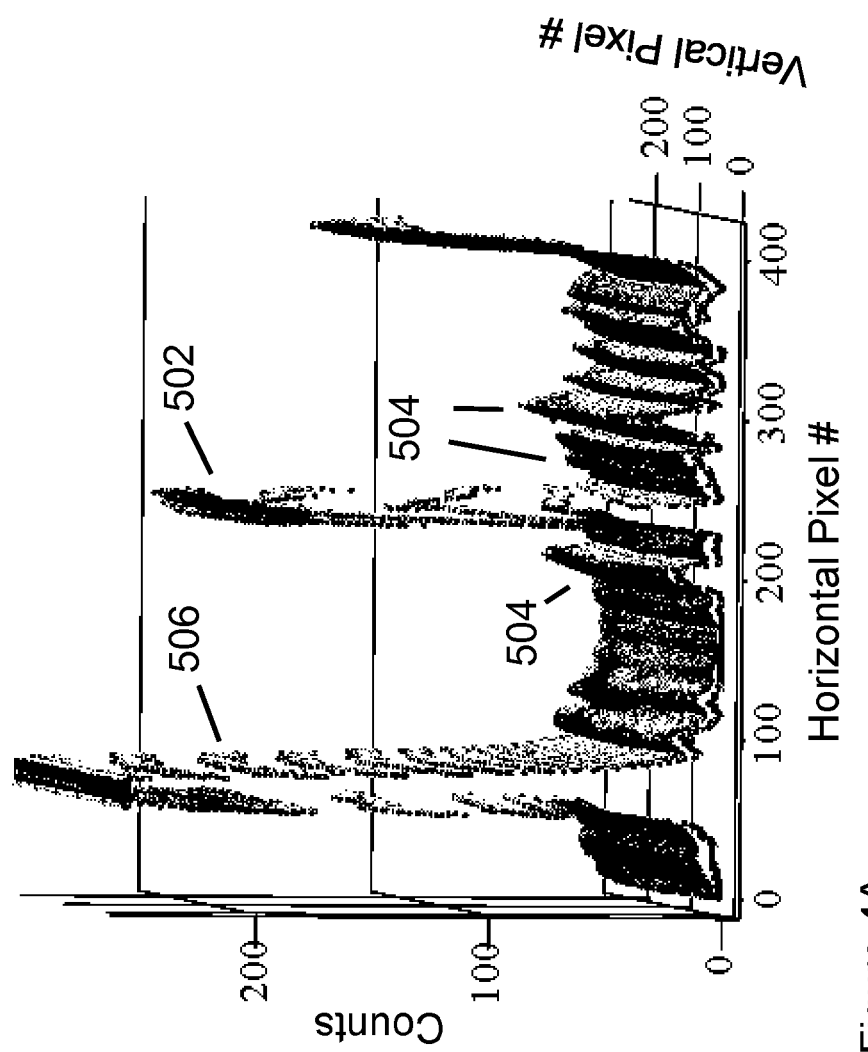
FIG. 4A illustrates the intensity of light that impinges on a camera that utilizes NIR optical beam.

FIG. 4A illustrates the intensity of light that impinges on a camera when the near-IR (NIR) optical beam of the refractive index measuring system is at a scan location where the deflection of the zero-order beam would be poorly resolved using the near IR measurement system. More specifically, FIG. 4A illustrates the intensity of light that impinges on a camera (vertical pixels 1-200) when the scanning beam is at a scan location where the deflection of the zero-order beam (502) is well resolved, and the scanning optical beam's wavelength $\lambda$=0.94 µm, and the detector operates in near-IR wavelength. In this embodiment the preform's striae separation d was 6.7 µm (i.e., thin pass preform, striae periodicity of 6.7 µm). The zero-order beam (502), the small angle diffraction (504) and the large angle diffraction (506) are detected as lines. The use of a slit has another advantage because its image spans the entire height of the camera. Hence a large number of pixels can be averaged by integrating along the axis of the image that is parallel to the long length of the slit image (along the vertical pixel axis), and this improves the signal to noise ratio in the integrated counts (FIG. 4B).

Figure 4B:
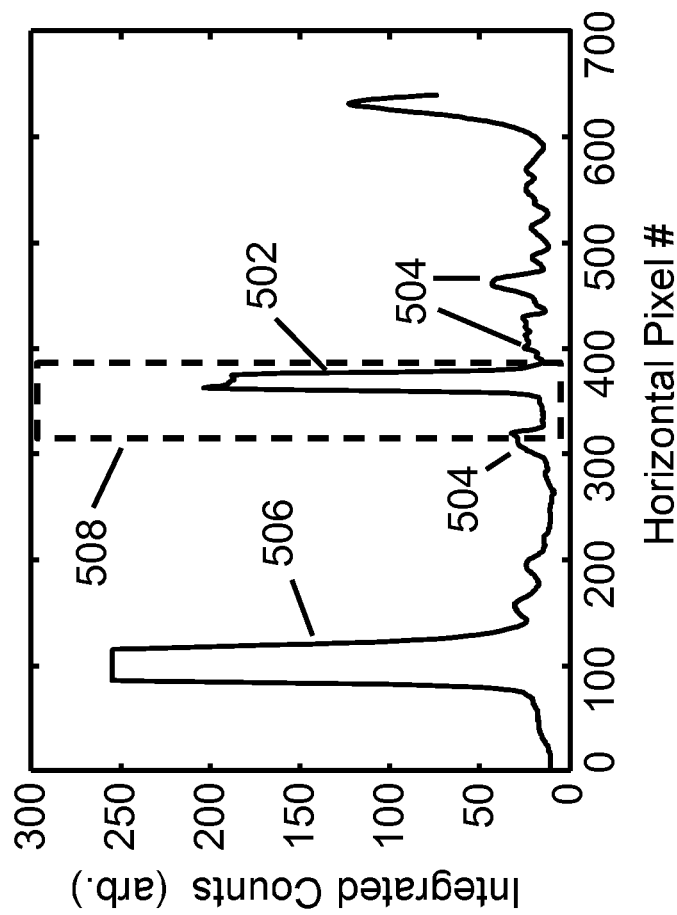
FIG. 4B illustrates the camera image data from FIG. 4A after it has been integrated along the vertical pixel axis direction (which is parallel to the long axis of the slit image and to the axis of the preform) to form an integrated intensity profile.

More specifically, FIGS. 4A and 4B illustrate the intensity of light that impinges on a camera when the measuring system (100) using NIR light is at the same a scan location where the deflection of the zero-order beam is poorly resolved when we are using the Mid-IR measurement system. In contrast it is well resolved using the NIR measurement system (same scan location). FIGS. 4A and B also show that in this embodiment the optical beams associated with the small angle diffraction 504, and the first-order diffraction 506 are well separated from the zero-order beam (502).

FIG. 4B illustrates the camera image data from FIG. 4A after integration along the vertical pixel axis direction (which is parallel to the long axis of the slit image and to the axis of the preform) to form an integrated intensity profile.

Figure 5A:
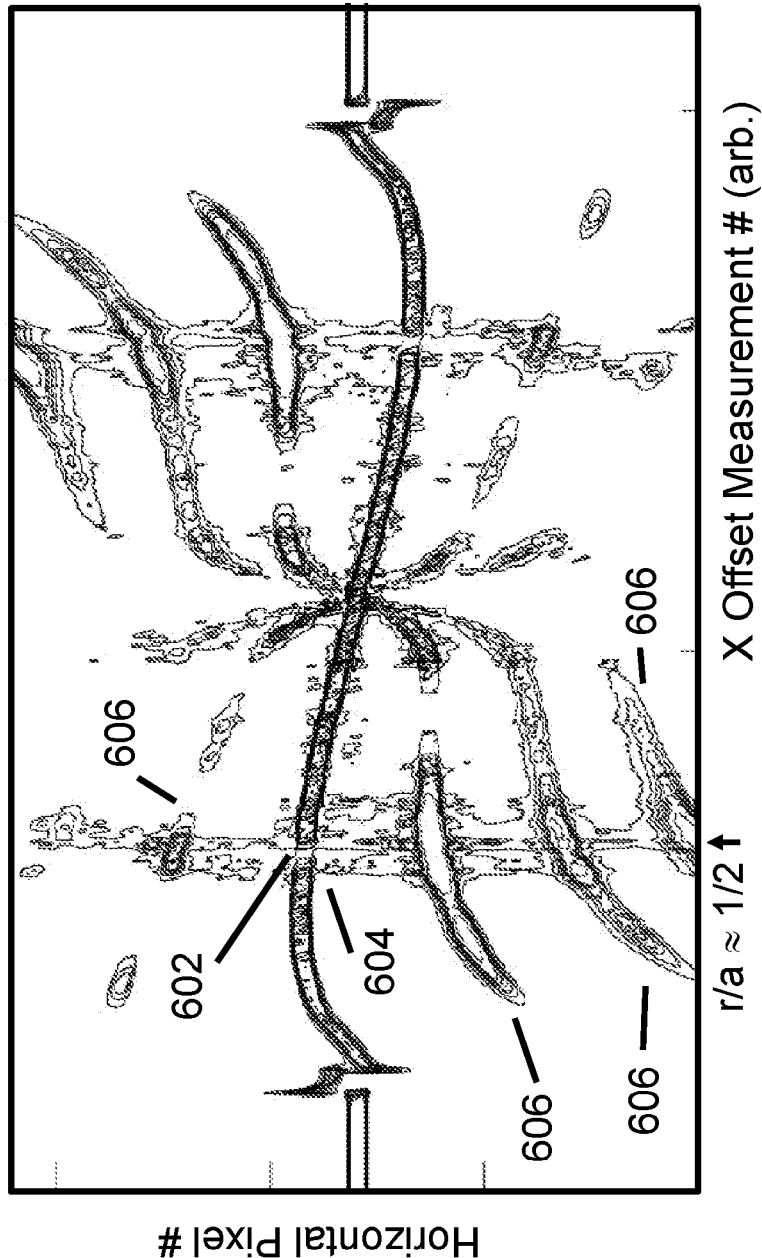
FIG. 5A is a contour plot comprised of the integrated intensity profiles at every sampling location $x_i$ in the scan of a thick pass preform, using the measurement system embodiment that operates at the NIR wavelength of 0.940 µm.

FIG. 5A shows the result of measuring a thick pass preform (d=14.1 µm) using the NIR measurement system of the embodiment when the measurement system employs just a single detector or camera 420. More specifically, FIG. 5A is a contour plot comprised of the integrated intensity profiles (expressed as digital integrated counts as a function of position on the detector) at every offset or sampling location $x_i$ (in this embodiment 1<i≤1100) in the scan of a thick pass preform using the exemplary system designed to operate at the NIR wavelength of 0.940 µm.

Figure 5B:
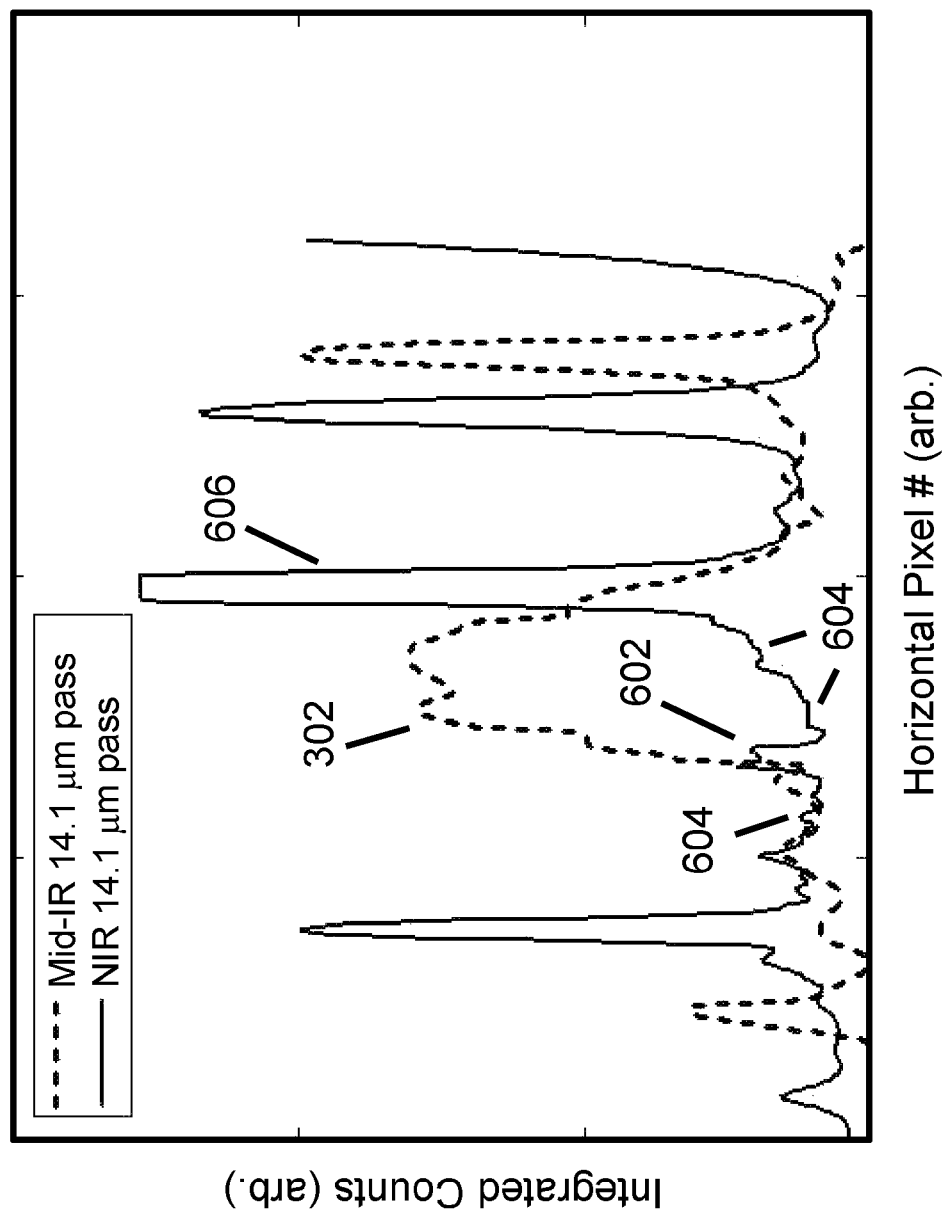
FIG. 5B illustrates an integrated intensity of light on a detector, corresponding to location of the cross-section of FIG. 5A (r/a=½), for an exemplary thick pass preform using a 0.940 µm light source (solid line) and for the exemplary thick pass preform using a 3.39 µm light source dashed line.

FIG. 5B compares the integrated intensity of the detector, as measured at the same radial location for the thick pass preform (e.g., d=14.1 µm) using a 0.94 µm light source in a NIR system (solid curve) and 3.39 µm light source in the Mid-IR system (dashed curve) at approximate location of r/a=½). When measured with the NIR system, the tracking of the zero-order beam (602) is nearly lost due to the large loss of optical power to small angle (604) and large angle diffraction (606). The integrated intensity data at this point (FIG. 5B) shows that power in the zero-order beam (602) is on the same levels as the small angle diffraction (604) and this creates a large error in the determination of the deflection angle and thus the refractive index profile. A comparison to the data obtained when measuring with the Mid-IR system shows less diffracted optical power and the location of the zero-order beam (302) is easier to determine. Hence the Mid-IR system may be more suitable for measuring refractive index profiles of thick pass preforms (d>12 µm) than the NIR system.

Figure 6A:
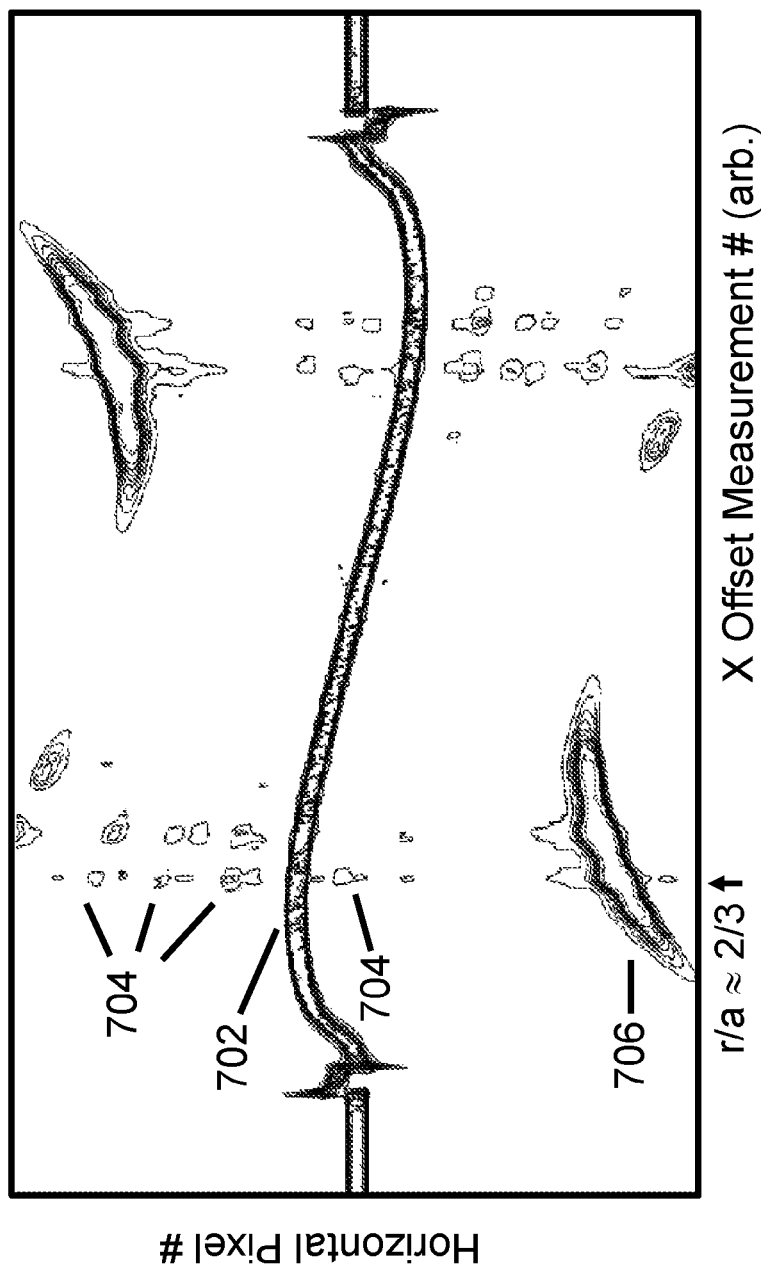
FIG. 6A illustrates data obtained using the exemplary NIR measurement system embodiment when performing a measurement on an exemplary preform made via OVD utilizing the thin pass process (striae separation d<10 µm)
Figure 6B:
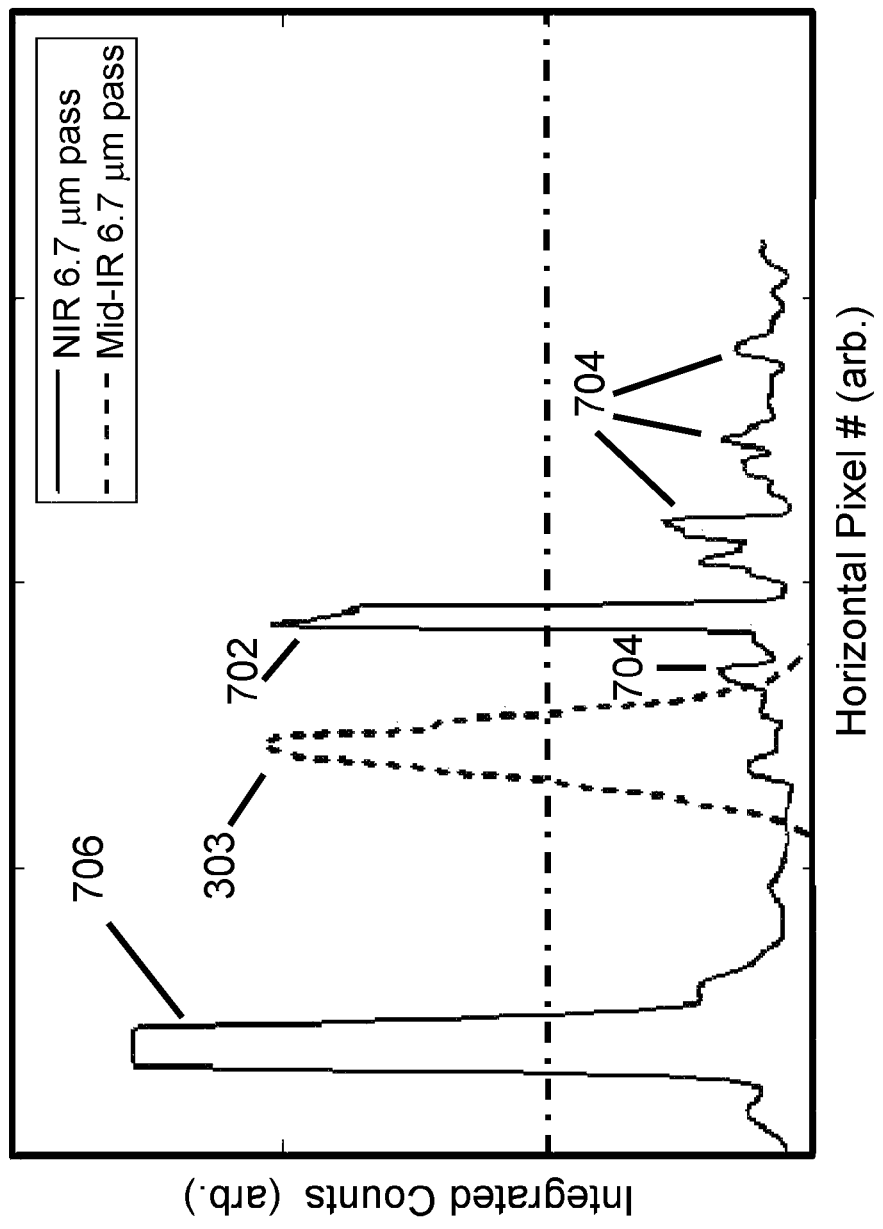
FIG. 6B illustrates the integrated intensity, data for a preform corresponding to the thin pass process using the Mid-IR measurement system (dashed line) and the NIR measurement system (solid line)

FIG. 6A illustrates data obtained using the NIR measurement system for the thin pass preform (consolidated glass layer thickness d<10 µm which corresponds to striae separation d<10 µm, e.g., in this embodiment d=6.7 µm). FIG. 6B illustrates the integrated intensity data on the detector, for a thin pass preform, using Mid-IR measurement system (dashed line) and the NIR measurement system (solid line) at the location r/a=⅔.

More specifically, FIG. 6A shows the results of measuring a thin pass preform (in this embodiment, 6.7 µm thick glass layers) using the NIR method of this embodiment of the present invention. FIG. 6A illustrates that the zero-order beam (702) is well defined. Small angle diffraction (704) is at a low level and though the large angle diffraction (706) is large, it is easily rejected from the analysis by the windowing technique and the zero-order beam is accurately measured. The integrated intensity profile (FIG. 6B) at the location where the diffraction is the worst (r/a=⅔) shows that the zero-order beam (702), the small angle diffraction (704) and the large angle diffraction (706) are well resolved and well separated from the zero-order beam, using the embodiment(s) described herein. A comparison is made with data obtained for a thin pass preform (layer thickness<12 µm, preferably <10 µm, (d<12 µm, preferably d<10 µm) as measured with the Mid-IR system (dashed curve), and shows the improved separation of the small angle diffraction from the zero-order beam (702) for the NIR measurement system (solid curve) as compared to the zero-order beam (303) measured in the MID IR system Since the effects of diffraction and those of power diffracted into higher orders scale as the ratio of d/$\lambda$, this method will work at shorter wavelengths when the striae periodicity is smaller. For example, in the measurement system operating at a wavelength of 600 nm, it would be advantageous when such a system is used to measure preforms with a striae periodicity of about 4-5 µm. For example, a measurement system operating at wavelength is 400 nm would be advantageous when used with a striae periodicity of about 2-4 µm (e.g., 2.5 µm, 2.9 µm, 3 µm, or 3.5 µm). Since the edge diffraction effect of the slit scales with wavelength, the slit width w' can be decreased and higher spatial resolution can be obtained in the measurement. For example, the consolidated optical preform may comprise silica doped with Germania, and may have striae, wherein the striae spacing is 1 µm≤d≤10 µm at or adjacent to the preform's radial position r, where r/a=½, and a is the outer radius of the preform.

Figure 7:
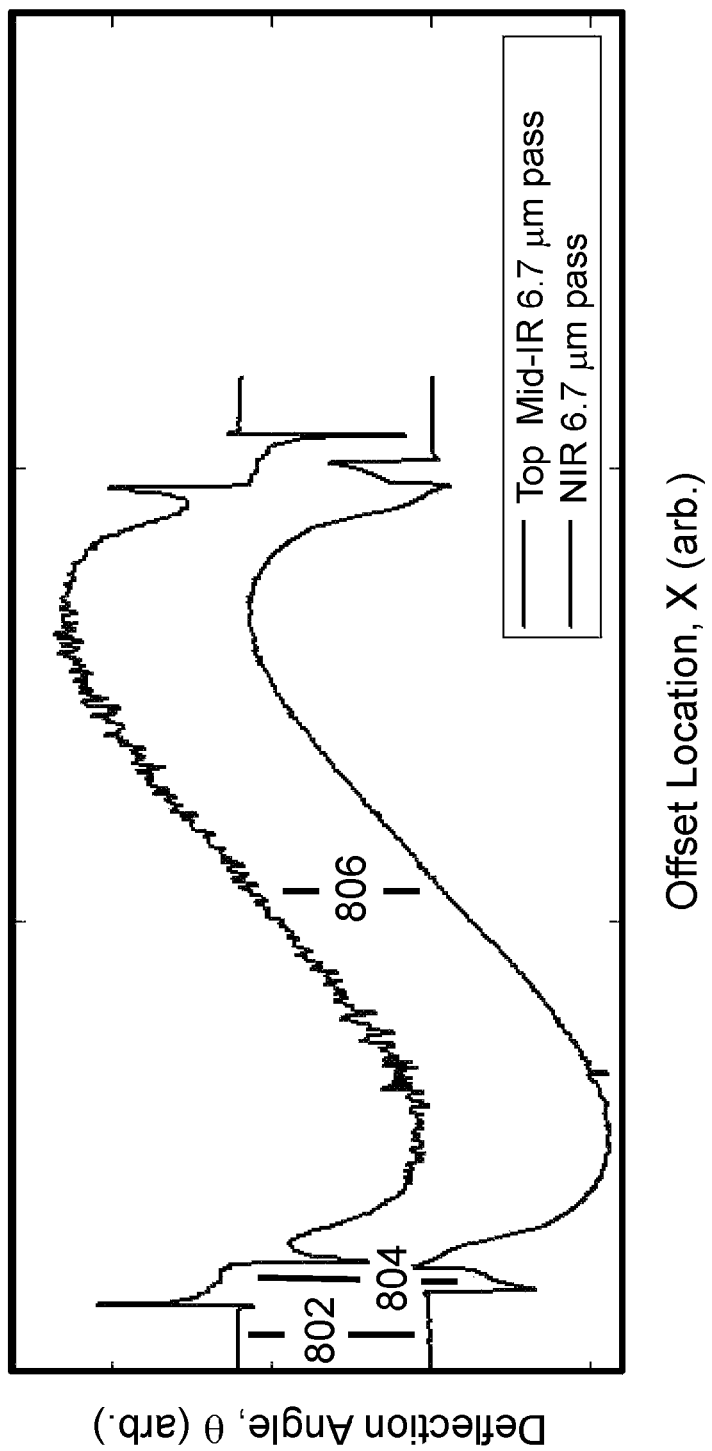
FIG. 7 illustrates the zero-order beam axis deflection angles that were obtained for the thin pass process using the Mid-IR measurement system (top) and the NIR measurement system (bottom).

FIG. 7 illustrates zero-order beam axis deflection angles that were obtained for the thin pass process (d=6.7 µm) using the Mid-IR measurement system (top) and the NIR measurement system (bottom). More specifically, this figure illustrates that the NIR measurement system provides more accurate beam deflection angle measurement (smoother curve), while the Mid IR measurement has more variability and thus is less smooth, and therefore is less accurate. More specifically, FIG. 7 shows the measured deflection angle function when the beam passes only through the silica cell (802), through the silica cell and the refractive index matching oil (804), and through the silica cell, the index matching oil and a thin pass preform (806) (layer thickness=6.7 µm) for both the Mid-IR system (top trace) and the NIR system (bottom trace) of the invention. The error in determining the zero-order deflection angle when passing through the preform is most evident by the variability in the central regions of both plots. Hence it can be seen that the NIR measurement system, having much less variability, will lead to a more accurate determination of the zero-order deflection angles of the scan and correspondingly a more accurate determination of the true refractive index profile of the preform.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. A method of measuring the refractive index profile of a consolidated glass body with a cylindrical surface, the method comprising the steps of:
   a. scanning the cylindrical surface of the consolidated glass body using an optical beam that emanates from an aperture, such that an image of the aperture is formed downstream from the consolidated glass body, between the consolidated glass body and at least one optical detector, and sampling the cylindrical surface with the optical beam at multiple sampling locations $x_i$;
      the multiple sampling locations $x_i$ being separated by distances $\Delta x$, such that $x_i = x_{i-1} + \Delta x$, with the image of the aperture having a width w, and $\Delta x < w$; wherein w is smaller than the diameter of the consolidated glass body;
   b. detecting locations where zero-order optical beams and corresponding to the sampling locations $x_i$ impinge on at least one optical detector after passing through the consolidated glass body;
   c. determining deflection angles of the zero-order beams corresponding to the multiple sampling locations $x_i$;
   d. calculating the refractive index profile of the consolidated glass body based on the deflection angles of the zero-order optical beams corresponding to the multiple sampling locations.

2. The method according to claim 1, the method further comprising the step of:
   predicting the trajectory of the zero-order optical beams through the consolidated glass body based on (i) the sampling locations $x_i$ of the optical beam impinging on the cylindrical surface of the consolidated glass body, and (ii) the locations at which the corresponding zero-order beams impinge on the at least one optical detector.

3. A method of measuring the refractive index profile of a consolidated glass body with a cylindrical surface, the method comprising the steps of:
   a. scanning the cylindrical surface of the consolidated glass body using an optical beam that emanates from an aperture, such that an image of the aperture is formed downstream from the consolidated glass body, between the consolidated glass body and at least one optical detector, and sampling the cylindrical surface with the optical beam at multiple sampling locations $x_i$;
   b. detecting locations where zero-order optical beams corresponding to the sampling locations $x_i$ impinge on at least one optical detector after passing through the consolidated glass body:
   c. determining deflection angles of the zero-order beams corresponding to the multiple sampling locations $x_i$;
   d. calculating the refractive index profile of the consolidated glass body based on the deflection angles of the zero-order optical beams corresponding to the multiple sampling locations,
   wherein
      the image of the aperture has a width w, wherein measurement sampling spacing $\Delta x$ across the cylindrical surface of consolidated glass body is less than or equal to w; and
      for each sampling location $x_i$ of the scan, where $x_i = x_{i-1} + \Delta x$, predicting a trajectory of the zero-order beam through the consolidated glass body based on sampling location $x_i$ of the optical beam impinging on the cylindrical surface and the location at which the zero-order beam is expected to impinge on the at least one optical detector; and
      discarding from final analysis data for higher order diffracted beams that are detected by the detector.

4. The method according to claim 3, wherein the step of calculating the refractive index profile of the consolidated glass body is performed by utilizing a transformation function which determines the refractive index at multiple locations within the consolidated glass body based on a deflection angle of the zero-order optical beam corresponding to one sampling location $x_i$ and the deflection angles of zero-order optical beams corresponding to prior sampling locations.

5. A method of measuring the refractive index profile of a consolidated glass body with a cylindrical surface, the method comprising the steps of:
   a. scanning the cylindrical surface of the consolidated glass body using an optical beam that emanates from an aperture, such that an image of the aperture is formed downstream from the consolidated glass body, between the consolidated glass body and at least one optical detector, and sampling the cylindrical surface with the optical beam at multiple sampling locations $x_i$;

b. detecting locations where zero-order optical beams corresponding to the sampling locations $x_i$ impinge on at least one optical detector after passing through the consolidated glass body;

c. determining deflection angles of the zero-order beams corresponding to the multiple sampling locations $x_i$;

d. calculating the refractive index profile of the consolidated glass body based on the deflection angles of the zero-order optical beams corresponding to the multiple sampling locations wherein the image of the aperture has a width w, wherein a measurement sampling spacing $\Delta x$ across the cylindrical surface of consolidated glass body is less than or equal to w; and for each sampling location $x_i$ of the scan, where $x_i = x_{i-1} + \Delta x$, predicting a trajectory of the zero-order beam through the consolidated glass body based on the sampling location $x_i$ of the optical beam impinging on the cylindrical surface and the location at which the zero-order beam is expected to impinge on the at least one optical detector; and discarding from final analysis data for small angle diffracted beams that are detected by the detector.

6. A method of measuring the refractive index profile of an optical fiber preform having a cylindrical surface comprising the steps of:

a. scanning the cylindrical surface of the optical fiber preform through multiple sampling location $x_i$ separated by distances $\Delta x$, such that $x_i = x_{i-1} + \Delta x$ with an illuminated slit such that an image of the slit is formed behind the optical preform, with the image of the slit having a width w, and $\Delta x < w$;

b. for each sampling location $x_i = x_{i-1} + \Delta x$, predicting a trajectory of the zero-order beam through the preform based on the sampling location $x_i$ of the optical beam impinging on the cylindrical surface of the optical preform and the location at which the zero-order beam is expected to impinge on at least one optical detector;

c. detecting the location where the exiting zero-order beams corresponding to sampling location $x_i$ impinge on at least one optical detector, and discarding data about higher order diffracted beams and small angle diffracted beams detected by the at least one optical detector for each sampling location $x_i$;

d. determining a deflection angle of the exiting zero-order beam corresponding to each sampling location $x_i$ of the scan;

e. calculating the refractive index profile of the preform by utilizing a transformation function which determines the refractive index at each sampling location $x_i$ based on the deflection angle of the beam corresponding to that location and other scanned sampling locations that are adjacent to $x_i$ but greater in distance from the center of the preform.

7. The method of claim 6, wherein said transformation function is an Abel transform.

8. The method of claims 6, wherein $w/8 \leq \Delta x \leq w/2$.

9. The method of claim 8, wherein said scanning is performed with a slit that is 100 µm to 25 mm long and has a width w' between 50 µm and 200 µm.

10. The method of claim 6, wherein: (a) the slit is between 100 µm to 25 mm long and has a tapered width w'(z) along the direction of the axis of the preform z, and 50 µm $\leq w' \leq 200$ µm, and the image of the slit has width w(z), and (b) sampling spacing $\Delta x$ between the multiple sampling locations $x_i$ is such that:

(⅛minimum slit width) $\leq \Delta x \leq$ (½minimum slit width).

11. The method of claim 10 further comprising illuminating the slit with a light source wherein the optical power provided by the light source is dynamically adjusted at each sampling location $x_i$.

12. The method of claim 6, wherein the image of the slit has a width w is 50 µm<w<200 µm, and consecutive sampling locations $x_i$ are separated by a distance $\Delta x$, where $\Delta x < w/2$.

13. The method of claim 6, further comprising illuminating the slit with a light source, wherein the optical power provided by the light source is dynamically adjusted at each sampling location $x_i$.

14. The method of claim 6, wherein the at least one optical detector is a silicon based detector or a NIR detector.

15. The method of claim 6, further comprising illuminating the slit with a light source, where the light source operates in the near-infrared (NIR) or visible light having a wavelength λ, the wavelength is 0.4 µm≤λ≤2 µm, has low coherence, with coherence length 0.001 mm≤l≤10 cm.

16. The method of claim 6, including utilizing two optical detectors for detecting locations of the zero-order optical beam, the two optical detectors are situated such that their object planes that are adjacent to the plane where the image of the aperture is formed.

17. The method of claim 16 wherein the object planes of the two optical detectors are situated by 0 mm to 5 mm offset from the aperture image plane and which are not in the same location.

18. The method of claim 6, whereby the preform is consolidated glass preform with striae spacing d from 1 to 15 µm, at or adjacent to the radial position r within the preform, where ⅓≤r/a≤⅔ and a is an outer radius of the preform.

19. The method of claim 18, wherein the preform comprises silica doped with Ge.

20. The method of claim 6, wherein the preform comprises silica doped with Ge.

* * * * *

UNITED STATES PATENT AND TRADEMARK OFFICE
CERTIFICATE OF CORRECTION

PATENT NO. : 9,989,458 B2
APPLICATION NO. : 14/928018
DATED : June 5, 2018
INVENTOR(S) : Ian David Cook et al.

Page 1 of 1

It is certified that error appears in the above-identified patent and that said Letters Patent is hereby corrected as shown below:

In the Claims

Column 23, Line 49, Claim 1, delete "method-of" and insert -- method of --, therefor.

Column 24, Line 30, Claim 3, delete "body:" and insert -- body; --, therefor.

Column 26, Line 6, Claim 8, delete "claims" and insert -- claim --, therefor.

Column 26, Line 16, Claim 10, delete "(⅛minimum" and insert -- (⅛ minimum --, therefor.

Column 26, Line 16, Claim 10, delete "(½minimum" and insert -- (½ minimum --, therefor.

Column 26, Line 18, Claim 11, delete "source" and insert -- source, --, therefor.

Column 26, Line 48, Claim 18, delete "⅓≤r/a≤⅔and" and insert -- ⅓≤r/a≤⅔ and --, therefor.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*